United States Patent [19]
Sandborn et al.

[11] Patent Number: 5,889,028
[45] Date of Patent: Mar. 30, 1999

[54] COLONIC DELIVERY OF NICOTINE TO TREAT INFLAMMATORY BOWEL DISEASE

[75] Inventors: William Sandborn, Rochester, Minn.; John Rhodes, Cardiff, Great Britain; Peter Rhodes, Wiltshire, Great Britain; Brian Kenneth Evans, South Glamor, Great Britain

[73] Assignee: Mayo Foundation for Medical Education and Research, Rochester, Minn.

[21] Appl. No.: 908,433

[22] Filed: Aug. 7, 1997

Related U.S. Application Data

[63] Continuation of Ser. No. 794,668, Feb. 3, 1997, abandoned, and a continuation-in-part of Ser. No. 605,319, Feb. 9, 1996, Pat. No. 5,846,983.

[51] Int. Cl.$^6$ .............................. A61K 9/02; A61K 9/32; A61K 31/465; A61K 31/78
[52] U.S. Cl. ........................ 514/343; 424/469; 424/474; 424/482; 424/486
[58] Field of Search ............................ 514/343; 424/469, 424/474, 482, 486

[56] References Cited

U.S. PATENT DOCUMENTS

| | | | |
|---|---|---|---|
| 3,877,468 | 4/1975 | Lichtneckert et al. | 131/2 |
| 3,901,248 | 8/1975 | Lichtneckert et al. | 131/2 |
| 4,855,142 | 8/1989 | Fankhauser et al. | 424/434 |
| 5,069,904 | 12/1991 | Masterson | 424/401 |
| 5,362,496 | 11/1994 | Baker et al. | 514/343 |
| 5,502,080 | 3/1996 | Hitzig | 514/654 |
| 5,512,306 | 4/1996 | Carlsson et al. | 426/3 |
| 5,549,906 | 8/1996 | Santus | 514/343 |
| 5,593,684 | 1/1997 | Baker et al. | 514/343 |
| 5,604,231 | 2/1997 | Smith et al. | 514/256 |
| 5,662,920 | 9/1997 | Santus | 424/435 |
| 5,721,257 | 2/1998 | Baker et al. | 514/343 |
| 5,783,207 | 7/1998 | Stanley et al. | 424/440 |

FOREIGN PATENT DOCUMENTS

| | | |
|---|---|---|
| 377520 | 7/1990 | European Pat. Off. |
| WO92/01457 | 2/1992 | WIPO |
| WO92/14452 | 9/1992 | WIPO |
| WO94/27576 | 12/1994 | WIPO |
| 97 28801 | 8/1997 | WIPO |
| 97 38726 | 10/1997 | WIPO |

OTHER PUBLICATIONS

Srivastava, E. D., et al, Eur. J. Gastroenterol., 3, 815–818 (1991).

Thomas, G. A. O., et al, Eur. J. Gastroenterol., 8, 769–776 (1996).

Lichtiger, S., et al, N. Engl. J. Med. 330, No. 26, 1841–1845 (Jun. 30, 1994).

Sandborn, W. J., et al, Gastroenterology, 108, 1429–1435 (1994).

Thomas, G. A. O., et al, N. Engl. J. Med., 332, No. 15, 988–992 (Apr. 19, 1995).

Lichtiger, S., et al, Gastroenterology, vol. 104, No. 4, Part 2, p. A732 AGA Abstracts (Apr. 1993).

Pullan, R. D., et al, N. Engl. J. Med., 330, No. 12, 811–815 (Mar. 24, 1994).

Zins, B. J., J. Clin. Pharmacol., 37, 426–436 (1997).

Sandborn, W. J., et al., "Transdermal Nicotine for Mildly to Moderately Active Ulcerative Colitis: A Randomized, Double–Blind Study, Placebo–Controlled Trial", presented at the annual meeting of the American Gastroenterology Association, May 20–22, 1996, San Francisco.

Sandborn, W. J., et al., Annals of Internal Medicine, vol. 126, No. 5, pp. 364–371 (Mar. 1997).

Cecil Textbook of Medicine, Wyngaarden, et al., eds., 19th edition, pp. 699–708, 1992, W. B. Saunders Company, Philadelphia.

Greenberg, G. R., et al., N. Eng. J. Med., vol. 331, No. 13, pp. 836–841 (Sep. 1994).

Anonymous, "Rectal Topical Corticosteroid Preparations", Drug and Therapeutics Bulletin 29, Publ. Consumer's Association, London, pp. 66–68 (1991).

Zins, B. J., et al., Gastroenterology, vol. 110, No. 4, p. A1054 (Apr. 1996).

Danish Budesonide Study Group, J. Gastroent., 1991, pp. 1225–1230.

Winder, T. A., et al., Scand. J. Gastroent. 28(8), pp. 701–704 (1993)—abstract only.

Handbook of Pharmaceutical Excipients, 2nd edition, p. 363.

*Primary Examiner*—Shep K. Rose

[57] ABSTRACT

A method is provided to treat inflammatory bowel disease by locally administering to the colon an effective amount of nicotine or a pharmaceutically acceptable salt thereof, preferably via formulations adapted for delayed oral release or rectal administration. Further provided is a novel formulation for the oral administration of nicotine comprising a polyacrylic polymer complexed with nicotine.

27 Claims, 11 Drawing Sheets

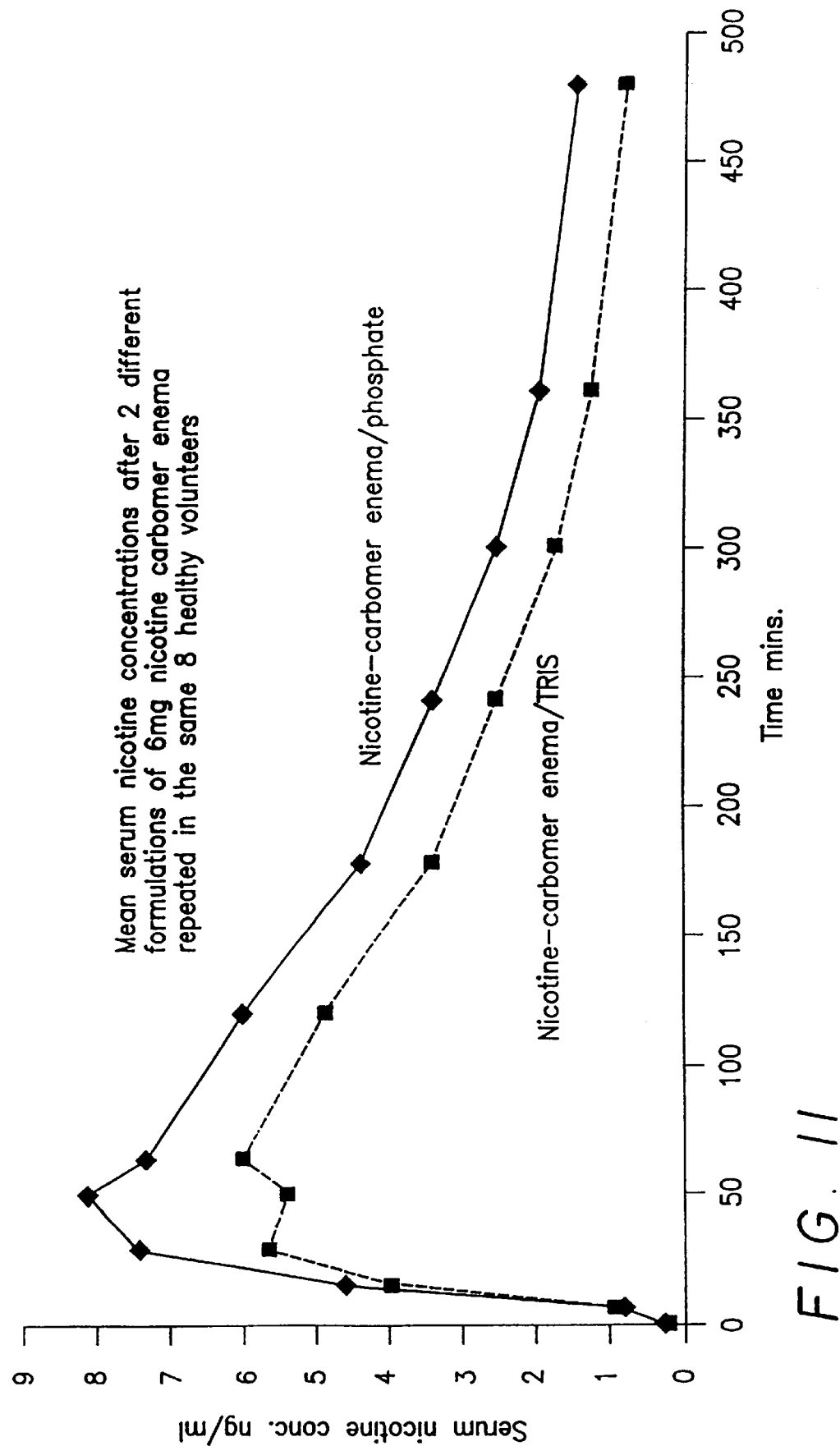

COLONIC DELIVERY OF NICOTINE TO TREAT INFLAMMATORY BOWEL DISEASE

CROSS-REFERENCE TO RELATED APPLICATIONS

This is a continuation of Ser. No. 08/794,668, filed Feb. 3, 1997, now abandoned and also a continuation-in-part of Ser. No. 08/605,319, filed on Feb. 9, 1996 now U.S. Pat. No. 5,846,983.

The invention was made with the support of Grant Nos. FD-T-000-886 and M01-RR00585 awarded by the U.S. Department of Public Health Services. The U.S. Government has certain rights in the invention.

BACKGROUND OF THE INVENTION

Inflammatory bowel disorders or diseases (IBD) encompass a spectrum of overlapping clinical diseases that appear to lack a common etiology. IBD, however, are characterized by chronic inflammation at various sites in the gastrointestinal (GI) tract. Illustrative IBD are regional enteritis (or Crohn's disease), idiopathic ulcerative colitis, idiopathic proctocolitis, pouchitis and infectious colitis. Symptoms of IBD may include persistent diarrhea, abdominal pain, fever, weight loss, joint pain, skin lesions and general fatigue. The inflammatory conditions of ulcerative colitis are confined to the colon, unlike Crohn's disease which can involve any portion of the intestinal tract.

Current treatment for IBD includes oral, IV and colonically administered corticosteroids and oral and colonically administered 5-aminosalicylic acid (Edsbacker et al., Gastroenterology 104:A695 (1993); Greenberg et al., NEJM 317:1625–29 (1987). Cyclosporin is another treatment for IBD, but this is limited to oral administration since colonic administration was not efficacious; (Gastroenterology 1994, 108:1429–1435).

Several types of colonic drug delivery systems are currently available, including enemas (Sutherland et al., Med. Clin. North Amer., 74:119 (1990)); rectal foams (Drug Ther. Bull., 29:66 (1991)); and delayed oral release formulations in the form of enteric-coated capsules which disintegrate at pH7 in the terminal ileum (Schroeder et al., NEJM, 317:1625 (1987)).

Carbomers have been shown to promote gel formation with mucin monomers from both gastric and colonic mucus (Pullan et al., Gut, 34:676–9 (1993)), and they may also inhibit fecal protease activity, which is responsible for mucolysis and solubilization of the adherent layer of mucus gel. This inhibition of mucolysis strengthens the colonic mucus barrier, which is deficient in ulcerative colitis and may play a role in its pathogenesis (Hutton et al., Clin. Sci., 78:265–71 (1990)).

Studies have suggested that an important epidemiologic link exists between ulcerative colitis (UC) and a patient's smoking history. Several investigators have reported that the prevalence of UC in non-smokers is higher than in current smokers. In addition, studies have suggested that ex-smokers are at even greater risk than life-time smokers for developing UC. It further appears that lifetime non-smokers exposed in childhood to passive tobacco smoke have a greater risk of developing ulcerative colitis than non-exposed lifetime non-smokers.

The observations that active colitis improves with smoking has led to investigational use of nicotine as a therapeutic agent. Since it would be unethical to ask patients to take up smoking, the nicotine was administered as polacrilex gum and a transdermal patch for the treatment of colitis (Roberts et al., Br. Med. J. 285:440 (1982); Srivastava et al)., Eur. J Gastro. & Hepat. 3:815–6 (1991): Pullman et al, The New England Journal of Medicine, March 1994, 811–815; Thomas et al. The New England Journal of Medicine, April 1995, 988–992). The great advantage of these routes of administration was like smoking a cigarette, the dose could be careful controlled and this was essential because of the highly addictive and toxic nature of nicotine. For example if the patient was feeling unwell, the patch could simply be removed. This was not an option with i.v. and oral formulations.

However, long term nicotine administration by way of polacrilex gum or transdermal patch proved to have limitations due to systemic side effects, as well as those inherent to the specific administration vehicles. For example, nicotine administered as chewing gum results in variable absorption and a wide range of plasma nicotine levels. Long term use of the transdermal patch is limited by a relatively high rate of dermatologic side effects. General side effects of nicotine administration reported in the aforementioned papers included nausea, vomiting, headaches, insomnia, somnolence, diaphoresis, pre-syncope and tremor, and in many cases forced the patient to withdraw from the treatment. In particular Pullman reported that three patients withdrew from treatment within three days because of intolerable side-effects, two more withdrew later, and the dosage had to be reduced in a further six patients. Thomas et al also reduced the dose of nicotine in the patch from 25 mg to 15 mg daily in an attempt to reduce the side effects to a tolerable level, but in the process lost the efficacy.

Thus, a need exists for a safe and effective method of treating IBD.

SUMMARY OF THE INVENTION

The inventors have now surprisingly discovered that nicotine delivered to the terminal ileum, rectum, and/or colon of a patient suffering from IBD is at least as efficacious as high dosage transdermal patch and substantially reduces the aforementioned side-effects which plagued the patch treatment. This is even more surprising because existing treatments such as cyclosporin which are very efficacious when given systemically fail completely when delivered colonically. Furthermore it would not be expected that an addictive and toxic agent such as nicotine whose side effects caused many patients to discontinue treatment could subsequently be reformulated to provide a safe and long term treatment substantially free of the previous side-effects.

The present invention provides a therapeutic method of treating inflammatory bowel disease (IBD) comprising locally administering to the rectum, colon and/or terminal ileum of a patient in need of such treatment, an amount of nicotine effective to reduce the symptoms of IBD. In one embodiment of the present method, the nicotine is administered orally, by means of a unit dosage form that selectively releases nicotine in the terminal ileum and/or colon of the patient. In another embodiment of the method, the nicotine can be effectively administered to the colon by rectal administration of an enema formulation or rectal foam comprising nicotine. Nicotine can also be delivered to the ileum or colon of an IBD patient by administration of an enterically coated unit dosage form. The present invention also provides a novel composition particularly suitable for the colonic administration of nicotine comprising crosslinked polyacrylic acid polymers complexed with nicotine.

Accordingly in a first aspect of the invention there is provided a nicotine or a pharmaceutically acceptable salt or derivative thereof in the preparation of a medicament for administering to the rectum, colon and/or terminal ileum of a patient for the treatment, prophylaxis, or maintenance of remission of inflammatory bowel disease.

By colon we mean to include the cecum, ascending colon, hepatic flexure, splenic flexure, descending colon, and sigmoid.

During studies with liquid enemas of nicotine bitartrate salt, the inventors found that the side effects were very limited if the patient lay on his side in the left lateral position, but increased if the patient adopted the sitting position. A preferred embodiment of the invention delivers nicotine as a complex of nicotine and polyacrylate which is much less dependent on the adopted position of the patient, and so increases the comfort of the patient during treatment. The nicotine-polyacrylate complex can be delivered rectally as an enema or foam, or orally as a post-gastrically delayed release product. Other nicotine containing post-gastrically delayed release tablets such as described herein are thought to also confer similar benefits.

In a particularly preferred embodiment of an enema comprising the nicotine-polyacrylate complex and triethanolamine (TRIS) as a buffer, the side-effects are further limited to a minimum.

By enema we mean to include liquid enemas which can be thickened by gums and the like, and foam enemas which expand in the colon after expulsion from a pressurised container.

DETAILED DESCRIPTION OF THE INVENTION

Nicotine is an organic compound which is derived from tobacco leaves, and comprises a pyridine (hydrophilic) and a pyrrolidine (hydrophobic) ring which enable it to form solutions in a wide variety of solvents including water, alcohol, ether, chloroform, kerosine and oils. The nicotine base (liquid at room temperature) is quite volatile and is readily absorbed through mucous membranes and intact skin. Nicotine salts (crystalline at room temperature), on the contrary, are very stable and not absorbed through the skin. For example, nicotine bitartrate salt consists of a single nicotine molecule in conjunction with two tartrate molecules and a single water molecule. This compound has been previously used in oral and IV pharmacokinetics trials (Miller et al., *Chest* 5:527 (1982); Benowitz et al., *Clin. Pharmacol. Ther.* 49:270 (1991)).

Any pharmacologically acceptable derivative or metabolite of nicotine which exhibits pharmacotherapeutic properties similar to nicotine may also be used in practicing the invention. Such derivatives and metabolites are known in the art (Glenn et al. *J. Org. Chem.*, 43:2860–2870 (1978); Dominiak et al., *Klin Wochenschr,* 63:90–92 (1985)) and include nicotine oxide and cotinine.

Any pharmaceutically acceptable acid or metal salt of nicotine may be used in practicing the present invention. A particular characteristic property of nicotine is its ability to form salts with almost any acid and double salts with many metals and acids. The acids that may be used to prepare the pharmaceutically acceptable acid salts of nicotine are those that form non-toxic acid salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluene sulfonate, camphorate and parmoate salts. Particularly preferred is the tartrate and bitartrate salts.

Although it is unknown how nicotine might act to treat ulcerative colitis, a number of possibilities exist. First, nicotine has been shown to suppress both humoral and cellular immunity and these immunosuppressive properties might have some therapeutic impact in ulcerative colitis.

Second, leukotriene mediated inflammation appears to be important in the pathogenesis of colitis. Nicotine appears to reduce mucosal production of eicosanoids including prostaglandin E, 6-keto-PGF1a, leukotriene B4. and leulkotriene C4/D4/E4.

Third, colonic mucous production has been shown to be qualitatively and quantitatively abnormal in patients with colitis. However, nicotine appears to increase mucus synthesis to levels observed in healthy subjects. In addition, rabbits receiving high doses of nicotine have greater mucus thickness as compared to controls.

Fourth, nicotine increases circulating ACTH and plasma cortisol. This increase in endogenous corticosteroids may have some beneficial effect on colitis. Interestingly, this effect is attenuated by exogenous steroid administration.

Finally, it has been reported that patients with ulcerative colitis have a significantly higher rectal blood flow than controls and that nicotine can reduce rectal blood flow to the normal range.

According to one preferred embodiment of the present method, nicotine is administered to the colon in the form of an enema formulation, which is rectally administered to the lower colon. Useful enema formulations comprise an effective amount of nicotine dissolved or dispersed in a suitable flowable carrier vehicle, such as water, alcohol or an aqueous-alcoholic fluid. The carrier vehicle is preferably thickened with natural or synthetic thickeners such as gums, acrylates or modified celluloses. The formulation can also comprise an effective amount of a lubricant such as a natural or synthetic fat or oil, i.e., a tris-fatty acid glycerate or lecithin. Nontoxic nonionic surfactanits can also be included as wetting agents and dispersants. Unit dosages of enema formulations can be administered from prefilled bags or syringes. The carrier vehicle may also comprise an effective amount of a foaming agent such as n-butane, propane or i-butane. Such formulations can be delivered from a preloaded syringe pressurized container, so that the vehicle is delivered to the colon as a foam, which inhibits its escape from the target site.

In a further preferred embodiment, nicotine is administered via oral ingestion. The effective amount of nicotine can be locally administered to the colon of the patient by oral ingestion of a unit dosage form such as a pill, tablet or capsule, comprising an effective amount of nicotine which is enterically coated so as to be released from the unit dosage form in the lower intestinal tract, e.g., in the ileum and in the colon of the patient. Enteric coatings remain intact in the stomach, but will dissolve and release the contents of the dosage form once it reaches the region where the pH is optimal for dissolution of the coating used. The purpose of an enteric coating is to substantially delay the release of the nicotine until it reaches its target site of action in the ileum or colon. Since nicotine locally administered to the colonic tissue in this fashion is only about 20% absorbed in the bloodstream (based on rectal administration), the systemic side-effects of nicotine can be avoided or minimized.

Aqueous film-coating technology is employed for the enteric coating of pharmaceutical dosage forms. Delayed-released oral nicotine dosage forms have the potential advantage of delivering nearly all the nicotine to the ileum or colon in an easily administered form which can theoretically avoid the increased systemic rectal absorption seen with enemas. In addition, enterically coated nicotine will not have the dermatologic side effects directly related to patch delivery.

Thus, a useful enteric coating is one that remains intact in the low pH environment of the stomach, but readily dissolved when the optimum dissolution pH of the particular coating is reached. This can vary between pH 3 to 7.5 depending upon the chemical composition of the enteric coating, but is preferably between about pH 6.8 and pH 7.2. The thickness of the coating will depend upon the solubility characteristics of the coating material and the site to be treated.

The most extensively used polymer for enteric coating is cellulose acetate phthalate (CAP). However, CAP has an optimum dissolution pH greater than 6, thus early drug release may occur. Another useful polymer is polyvinyl acetate phthalate (PVAP) which is less permeable to moisture and gastric fluid, more stable to hydrolysis and able to dissolve at a lower pH, which could also result in early release of nicotine in the duodenum.

Another available polymer is hydroxypropyl methylcellulose phthalate. This has similar stability to PVAP and dissociates in the same pH range. Further examples of currently used polymers are those based on methacrylic acid, e.g., methacrylic acid ester copolymers with acidic ionizable groups, such as Eudragit L, S or LS and mixtures thereof, the choice dependent upon the site of required dissolution of the coating. Dosage forms coated with Eudragit, which dissolve in the ileum at about pH 6.8., and in the terminal ileum and caeceum at about pH 7.2., have been developed for the delivery of 5-aminosalicylic acid, and can be used in accordance with the present invention.

In general coating thicknesses of about 25 to 200 $\mu$m, and especially 75 to 150 $\mu$m, are preferred using about 3 to 25 mg, preferably 8 to 15 mg of acidic coating material per cm$^2$ of tablet or capsule surface. The precise coating thickness will however depend upon the solubility characteristics of the acidic material used and site to be treated.

A sustained-release formulation can be achieved by either using a microgranular formulation of the nicotine compound coated with semi-permeable membrane such as ethylcellulose or by coating the granules with a lacquer consisting of an acrylic resin based on acrylic and methacrylic acid esters containing a low content of quaternary ammonium groups at a predetermined molar ratio. Suitable resins include Eudragit RL and RS. The coated granules may then be compressed into tablets or packed into hard gelatin capsules suitable for oral administration.

A dosage form of nicotine adapted for either rectal or oral delivery may also be complexed with a suspending or thickening agent to prolong release of the dosage form of nicotine. A particularly preferred embodiment of the invention includes acrylic acid polymers, preferably carbomers (carboxypolymethylene) which are synthetic high molecular weight acrylic acid polymers crosslinked with polyfunctional moieties such as polyallylsucrose. Generally, carbomers comprise 50 to 70% carboxylic acid groups.

When used in accordance with an oral dosage form of the invention the carbomers hydrate and swell to form a gel, which retards the nicotine release and absorption. The nicotine-carbomer complex is mucoadhesive and adheres to the colonic mucus thereby potentially maximizing the nicotine/carbomer effect on the colonic mucosa but limits systemic absorption.

Carbomers are available as fine white powders which disperse in water to form acidic colloidal suspensions (a 1% dispersion has approx. pH 3) of low viscosity. Neutralization of these suspensions using a base, for example sodium, potassium or ammonium hydroxides, low molecular weight aminies and alkanolamines, results in the formation of clear translucent gels. Nicotine salts such as nicotine chloride form stable water-soluble complexes with carbomers at about pH 3.5 and are stabilized at an optimal pH of about 5.6.

In one embodiment of the invention, the carbomer is Carbopol. Such polymers are commercially available from B. F. Goodrich under the designation Carbopol 420, 430, 475, 488, 493, 910, 934, 934P and the like. Carbopols are versatile controlled-release polymers, as described by Brock (*Pharmacotherapy*, 14:430–7 (1994)) and Durrani (*Pharmaceutical Res.* (*Supp.*) 8:S-135 (1991)), and belong to a family of carbomers which are synthetic, high molecular weight, non-linear polymers of acrylic acid, crosslinked with polyalkenyl polyether. In a particularly preferred embodiment the carbomer is Carbopol® 974P NF.

To prepare nicotine/carbomer complexes, the carbomer is suspended in an appropriate solvent, such as water, alcohol or glycerin. Preferably, the carbomer is mixed with water, preferably de-ionized water. Mixtures may range, for example, from 0.002 to 0.2 grams of carbomer per mL of solvent, preferably from 0.02 to 0.1 grams of carbomer per mL of solvent. The mixture is stirred thoroughly at room temperature until a colloidal suspension forms. The dispersion may be stirred using a suitable mixer with a blade-type impeller, and the powder slowly sieved into the vortex created by the stirrer using a 500 micron brass sieve. This technique allows ample wetting of the powder and prevents the powder from forming a cluster of particles which then become difficult to wet and disperse.

The nicotine or nicotine salt may be diluted with any pharmaceutically acceptable organic solvent. In a preferred embodiment, the solvent is an alkanol such as ethanol. Mixtures may range, for example, from 0.01 to 10 grams of nicotine per mL of solvent, preferably from 0.5 to 5 grams of nicotine per mL solvent. This solution is then added drop wise to the carbomer suspension and mixed continuously until a gel of uniform consistency has formed. Preferably, the nicotine/complex is made by combining 1 gram of nicotine or nicotine salt with from 0.1 to 100 grams of carbomer, more preferably with 1 to 50 grams of carbomer. A gradual thickening of the suspension may occur as neutralization of the carbomer takes place. The complex will also become white. This physical change in viscosity is consistent with neutralization of the acid by the base.

The gel is then dried. According to one embodiment, the gel is vacuum dried. By way of example, the gel is spread on a glass plate and dried under vacuum at 50° C. for about 24 hours. Alternatively, the gel may be freeze-dried. Such methods are well known in the art.

Nicotine/carbomer complexes can then be formed into solid dosage forms and a pharmaceutically acceptable coating may be applied, as described above for non-complexed nicotine. For example, the complex may be enterically coated thereby delaying the release of the nicotine/carbomer complex until it reaches the ileum and colon; and thus maximizing its local effect on the colon. The nicotine/carbomer complex will likely not be absorbed and this theoretically will prolong and enhance the effect of nicotine on the colonic mucosa. The capsule may be coated with a Eudragit film and the contents themselves coated either as a powder or as microgranules or microspheres.

In addition to being orally administered, the nicotine/carbomer complexes may be administered rectally as liquid enemas. Liquid enemas are prepared essentially as described above by adding an effective amount of a nicotine/carbonier complex to a suitable flowable liquid carrier The carrier vehicle is preferably thickened with thickeners and can also comprise an effective amount of a lubricant. Unit dosages of enema formulations can be administered from prefilled bags or syringes. Carbomers alone may have some therapeutic role in ulcerative colitis, when given as an enema.

It will be appreciated that the amount of nicotine, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, where the nicotine is administered rectally, a suitable dose will be in the range of from about 0.001 to about 1.5 mg/Kg, preferably in the range of 0.01 to 0.20 mg/Kg, most preferably in the range of 0.04 to 0.10 mg/Kg, calculated as nicotine in the free base form. Preferably, nicotine is rectally administered once or twice daily.

Based on an average 70 kg patient, the average daily dose of nicotine is preferably from about 0.07 mg to 105 mg, more preferably about 0.7 mg to about 36 mg, more preferably still in the range of about 0.7 mg to about 14 mg, more preferably still about 1 mg to 12 mg, more preferably still in the range of about 3 mg to about 7 mg, and most preferably about 6 mg.

In general, where the nicotine is administered orally, a suitable dose will be in the range of from about 0.001 to about 1.5 mg/Kg, preferably in the range of 0.01 to 0.20 mg/Kg, most preferably in the range of 0.04 to 0.10 mg/Kg, calculated as nicotine in the free base form. Preferably, nicotine is orally administered 1 to 4 times daily, more preferably 3–4 times daily, although more frequent dosing is contemplated where hourly dosing is desired. For a 70 kg patient, the above mentioned average daily dosages also apply.

The compound is conveniently administered orally in unit dosage form; for example, containing 0.10 to 20 mg, conveniently 0.5 to 10 mg, most conveniently, 3 to 6 mg of active ingredient per unit dosage form.

The above doses apply both to treatment of active IBD and in the maintenance of remission.

Studies described herein compare the bioavailability and pharmacokinetics parameters of nicotine after administration by each of 6 different routes: IV; oral; hydrophilic enema (acidic and basic); and hydrophobic enema (acidic and basic). Thirty (30) healthy volunteers were enrolled in this prospective randomized study. All subjects underwent 2 investigations (IV and non-IV) at least one week apart. Subjects were divided equally among the 5 non-IV groups: hydrophilic rectal enema (acidic or basic); hydrophobic rectal enema (acidic or basic); and oral. Plasma nicotine concentrations were measured before and during the 8 hour period following administration.

The mean bioavailability for the oral route was 19 (10%); the mean bioavailability for rectal enemas were: hydrophilic acidic 16 (7%); hydrplilic basic 14 (6%); hydrophobic acidic 25 (7%): and hydrophobic basic 15 (4%). There was no statistical difference in bioavailability between the 5 delivery routes and all 5 were significantly less than the bioavailability for IV nicotine 100 (0% (p<0.01). Side effects directly correlated with plasma nicotine concentrations. Thus, oral and colonic administration of nicotine had low or negligible bioavailability and was well tolerated.

The invention appears to be most efficacious on life-long non-smokers, or smokers who had stopped smoking, although it can also be of benefit to heavy smokers and intermittent smokers. This is particularly so because the nicotine can be delivered in therapeutic doses without causing intolerable side-effects. Although all patients suffering from IBD should benefit from the invention, the treatment is of particular benefit in patients with severe ulcerative colitis which is unresponsive to conventional first-line therapies such as corticosteroids and 5-ASA. As well as treatment of active disease, the invention can also be used to treat patients in remission.

Although the invention can be used as a monotherapy for IBD, the inventors' findings have shown that it is particularly good and appears to show a synergistic effect when administered concomitantly with 5-ASA (mesalazine), sulphasalazine, alsalazine, prednisolone (and other corticosteroids), or budesonide.

Accordingly a further aspect of the invention relates to a pharmaceutical combination product comprising nicotine or a salt or a pharmaceutically acceptable derivative thereof adapted for delivery to the return terminal ileum and/or colon, and a compound selected from 5-ASA, sulphasalazine, asalazine, prednisolone, or budesonide for simultaneous, separate, or sequential administration.

The invention will be further described by reference to the following detailed examples and drawings.

BRIEF DESCRIPTION OF THE DRAWINGS

FIGS. 10 and 11 show the nicotine plasma level over time with three types of enema according to the invention (a) nicotine tartrate (Example 4), (b) nicotine-carbomer with phosphate buffer (Example 3) and (c) nicotine-carbomer with TRIS buffer (Example 5).

EXAMPLES

Example 1

Figure 1:
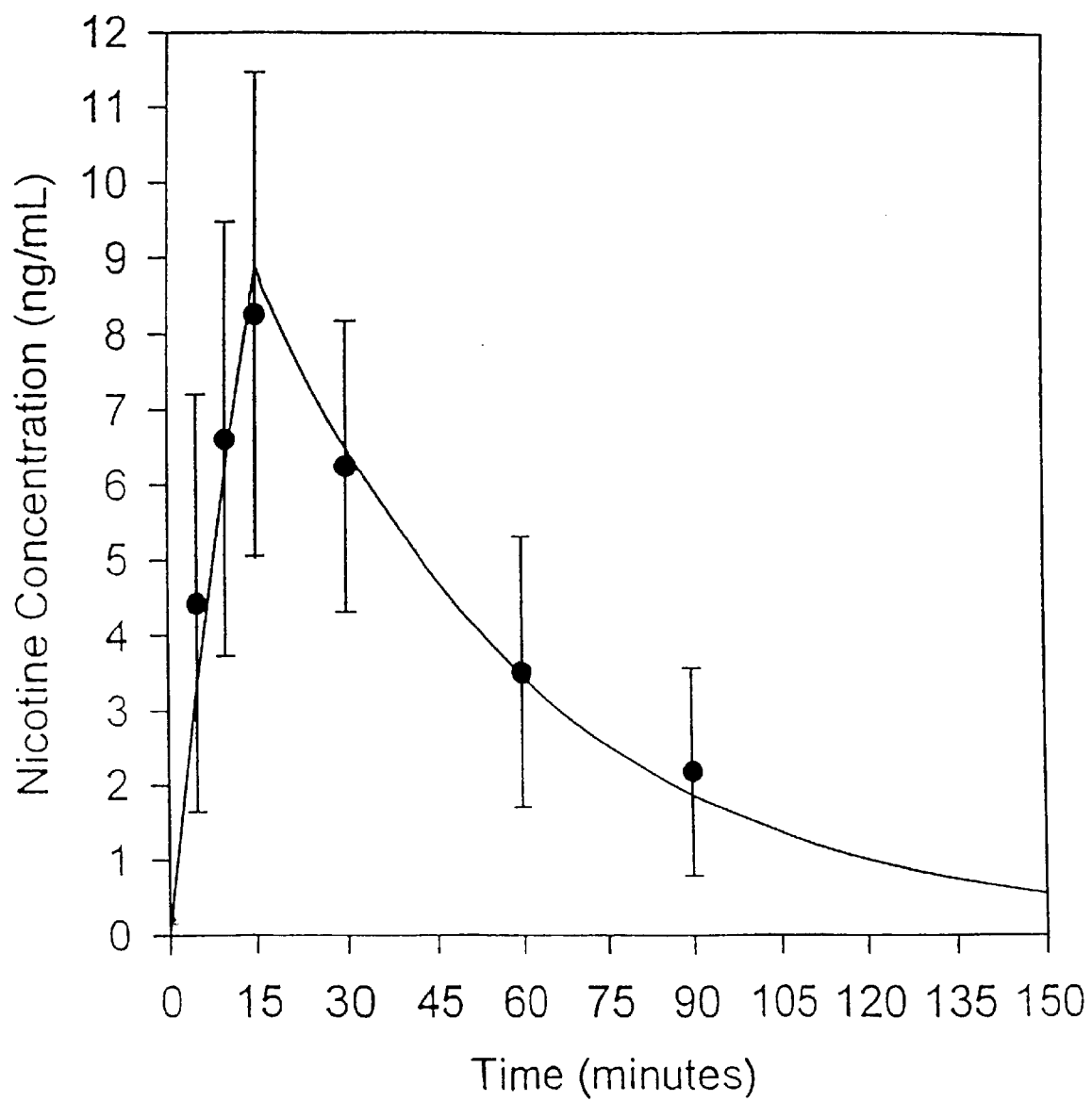
FIG. 1 shows mean plasma concentration-time curve during intravenous administration of 15 mcg nicotine/Kg body weight over 15–30 minutes.
Figure 2:
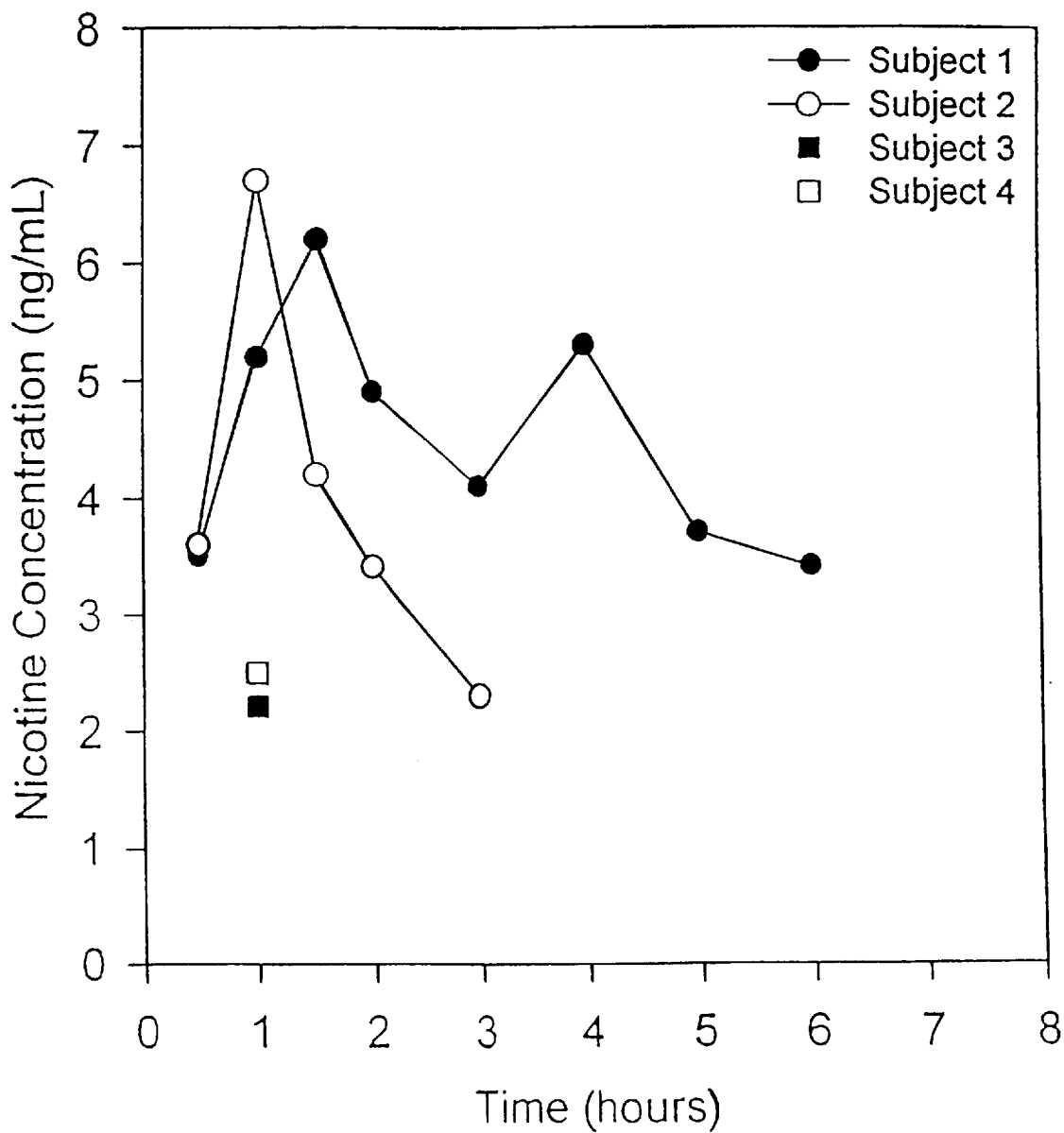
FIG. 2 shows plasma concentration-time curve after oral administration of 45 mcg nicotine/Kg body weight for each subject with detectable levels (2 subjects had no detectable levels).
Figure 3:
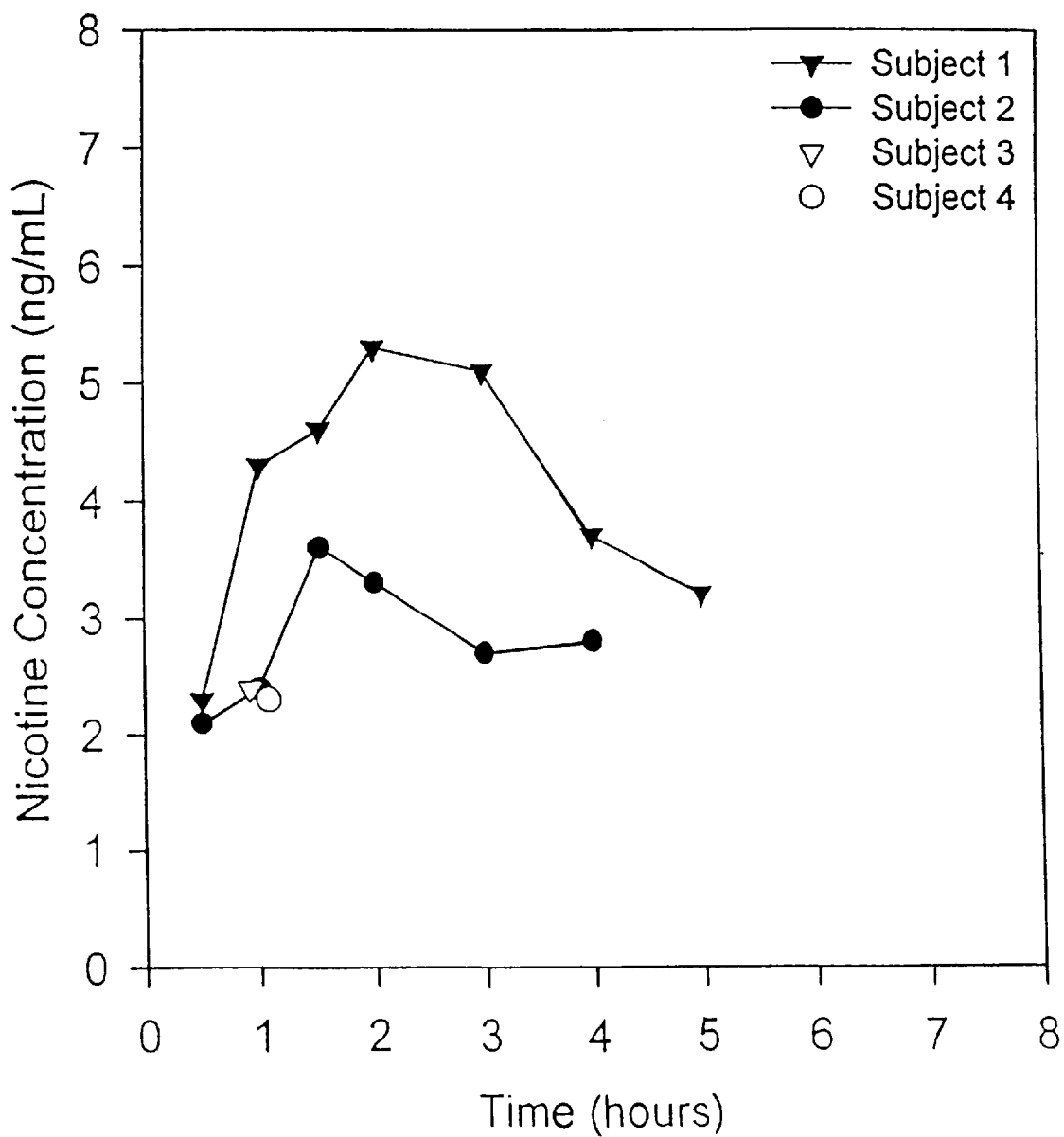
FIG. 3 shows plasma concentration-time curve after administration via hydrophilic acidic enema vehicle of 45 mcg nicotine/Kg body weight for each subject with detectable levels (2 subjects had no detectable levels).
Figure 4:
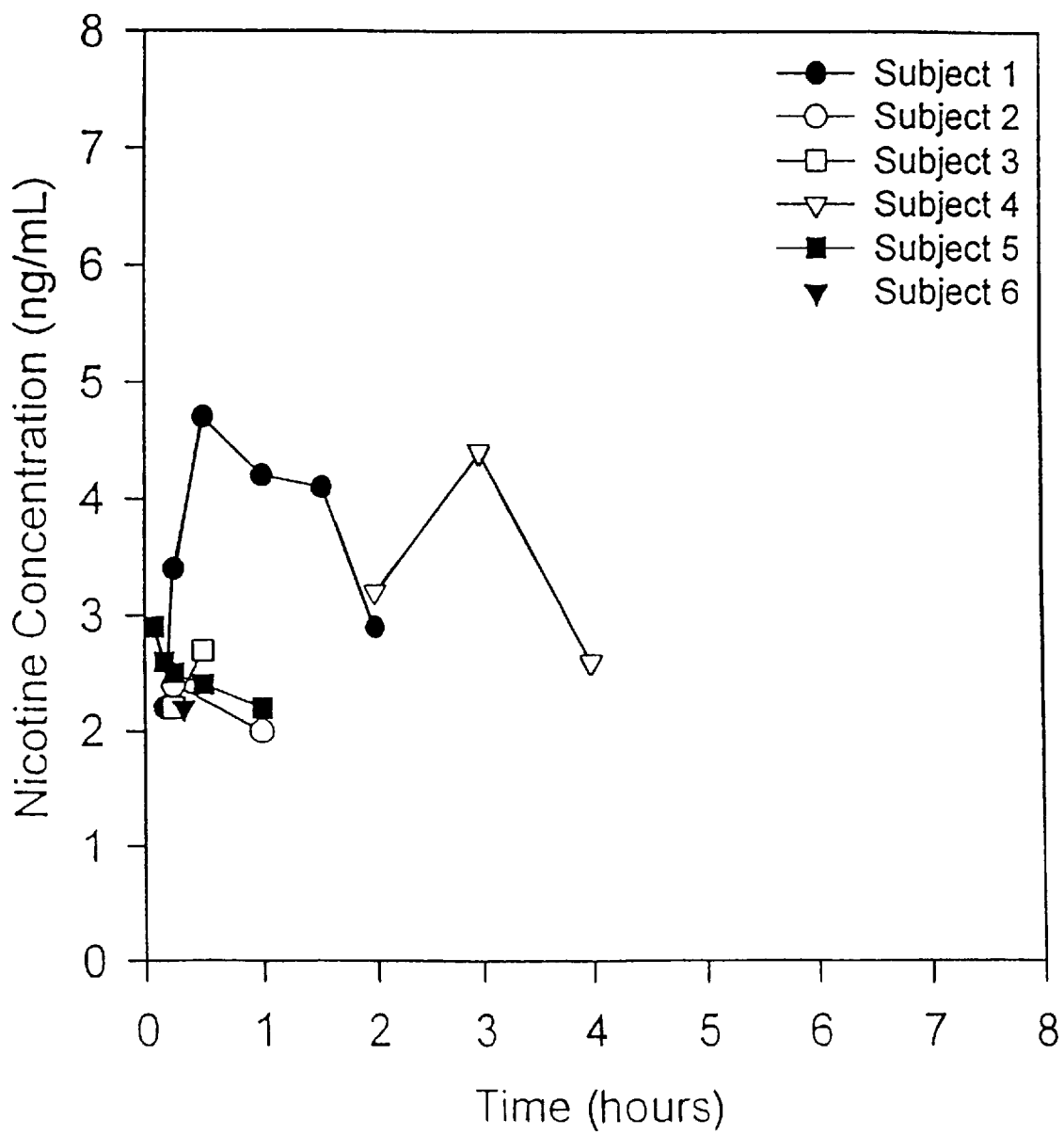
FIG. 4 shows plasma concentration-time curve after administration via hydrophilic basic enema vehicle of 45 mcg nicotine/Kg body weight for each subject with detectable levels (1 subject had no detectable levels).
Figure 5:
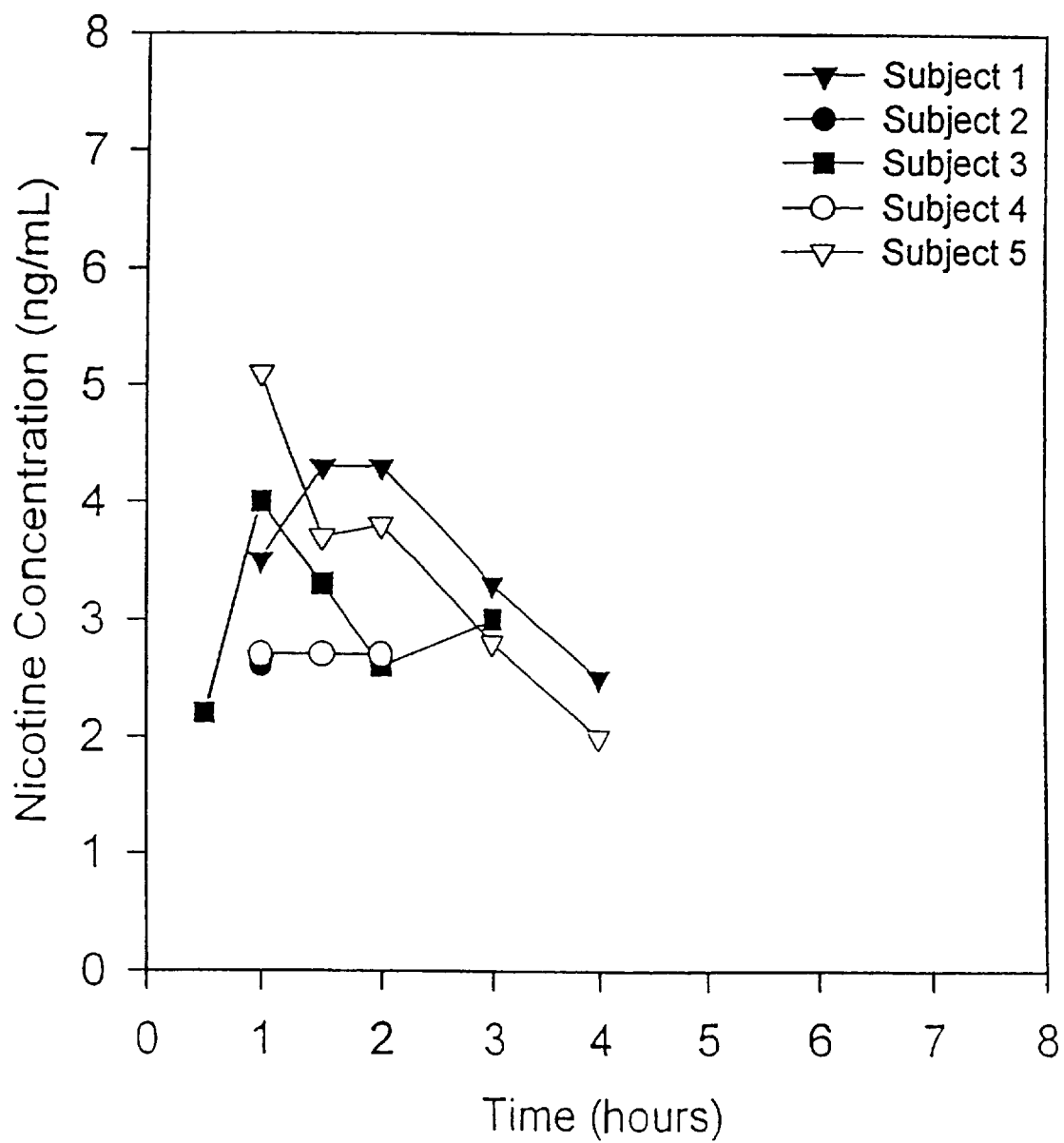
FIG. 5 shows plasma concentration-time curve after administration via hydrophobic acidic enema vehicle of 45 mcg nicotine/Kg body weight for each subject with detectable levels (1 subject had no detectable levels).
Figure 6:
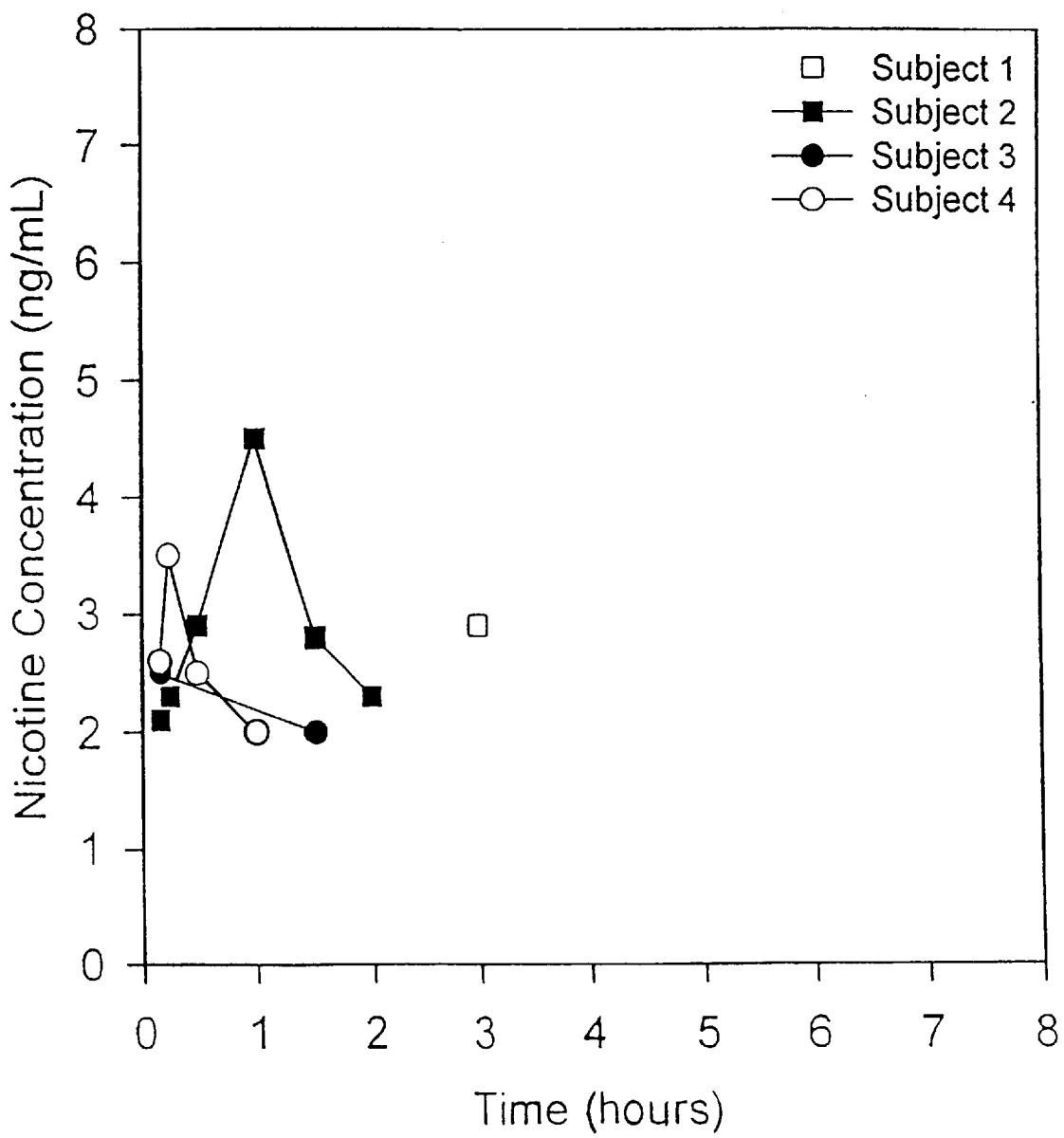
FIG. 6 shows plasma concentration-time curve after administration via hydrophobic basic enema vehicle of 45 mcg nicotine/Kg body weight for each subject with detectable levels (2 subjects had no detectable levels).

This study compared the bioavailability and pharmacokinetics parameters of nicotine after administration by each of 6 different routes: IV; oral; hydrophilic enema (acidic and basic); and hydrophobic enema (acidic and basic).

Intravenous nicotine was prepared using a nicotine base, supplied as the tartrate salt (Fisher Scientific/Eastman Kodak Company, Rochester, N.Y.). Solutions for injection were made up by combining 1.5 mg nicotine base (4.44 mg tartrate salt) in 100 ml of 0.9% sterile normal saline to form a 15 mcg/mL solution. The intravenous solution was filtered through a 0.22 micron filter into a sterile container and under sterile conditions. The solution was then cultured for organisms, assayed for endotoxin, and chemically analyzed prior to infusion to assure stable nicotine concentration. These samples were then be stored in sealed vials until the time of administration.

The oral preparation was formed by dissolving 45 micrograms nicotine base/kg body weight (133.3 micrograms tartrate salt/kg body weight) in 30 ml purified water. This dosage (approximately 3 mg nicotine base for a 70 kg, subject) has been well-tolerated in a previous study in which oral nicotine was administered (Benowitz et al., *Clin. Pharmacol. Ther.* 49:270–7 (1991)).

The hydrophilic enema vehicle was prepared by combining 500 mg of medium viscosity carboxymethylcellulose (Spectrum Chemical Manufacturing Corporation, Gardina, Calif.), 5 g sorbitol (Spectrum Chemical), and 60 mL of water. The sorbitol was added to make the vehicle isoosmolar and the carboxymethyl cellulose was used as a suspending agent. The vehicle, described previously (Sandborn et al., *J. Clin. Pharmacol.* 31:76–80 (1991)), was dispensed into 120 ml enema bottles. The active agent, 133.3 micrograms nicotine tartrate salt/kg body weight (equivalent to 45 micrograms nicotine base/kg body weight) was added to the enema vehicle.

The hydrophobic enema vehicle was prepared by adding 3 g of Witepsol H-15 (an oleaginous base—Huls American Inc., New Jersey) to the hydrophilic enema vehicle. Enema vehicles were made acidic by adding 5.06 g of sodium citrate dihydrate (Spectrum Chemical) and 0.56 g of citric acid monohydrate (Spectrum Chemical) to create a solution with a pH of 5.5. Enema vehicles were made basic by adding 5.23 g of sodium phosphate (Spectrum Chemical) and 0.05 g of sodium phosphate monobasic (Spectrum Chemical) to create a pH 8.5 solution. The enema vehicles were confirmed to be stable over a 48 hour time period (100% recovery) with a minimal decrease in nicotine concentration when allowed to stand at room temperature over a 3 week period (97% recovery at 1 week, 94% recovery at 2 weeks, 91% recovery at 3 weeks).

Thirty paid human volunteers were admitted to the pharmacokinetic study after giving informed consent to a protocol approved by the institutional review board at the Mayo Clinic, Rochester, Minn. The subjects ranged in age from 21–56 and their body weights ranged from 45 to 153 Kg. All subjects were non-smokers and were healthy based on their histories, and physical examination. Subjects agreed to practice birth control during the study period. Complete blood count, chemistry group, urinalysis and pregnancy test (women only) were obtained. Subjects were excluded if they had cardiovascular disease, peripheral vascular disease, hypertension, were nursing mothers, had laboratory evidence of pregnancy, or had hepatic or renal dysfunction.

Based on the results of a pilot study of two additional subjects, it was determined that colonic absorption of nicotine is dependent upon patient position, with higher plasma levels detected when subjects were allowed into a sitting position immediately after administration, rather than remaining in the left lateral decubitus position. The first subject studied underwent 3 investigations (IV, 15 mcg/Kg hydrophilic basic enema, 45 mcg/Kg hydrophilic basic enema). During the 15 mcg/Kg enema visit the subject was inadvertently allowed into a sitting position after administration and was found to have an AUC of 17 (ng)(hr)/mL (IV visit AUC 18 (ng)(hr)/mL) with a bioavailability of 94%. On the 45 mcg/Kg visit the subject remained in the left lateral decubitus position the entire time the enema was retained and had an AUC of 0 (ng)(hr)/mL with a bioavailability of 0%. Similarly, one subject withdrew from the study after the enema visit (first visit) in which an upright position was taken shortly after administration and side effects occurred. The AUC for this subjects visit was 18 (ng)(hr)/ml. During the remainder of the study, subject position was more closely monitored and plasma nicotine concentrations remained low or undetectable with enema administration.

Each subject underwent 2 investigations (IV and non-IV) of 8 hours duration at least 1 week apart. During the IV visit, subjects were given a 15–30 minute infusion of the IV nicotine solution (15 mcg/Kg dose). During the non-IV visit subjects were given a 45 mcg/Kg dose of nicotine base via one of five randomly selected delivery routes which were prepared within 48 hours of administration: oral; hydrophilic enema (acidic or basic); hydrophobic enema (acidic or basic). The subjects were instructed to remain in the left lateral decubitus position while the enema was retained and to retain the enema for at least one hour. On each study day, venous blood samples were drawn from an IV catheter into standard chemistry vacutainer tubes. Samples were obtained before nicotine administration and at the following time points (time=0 was defined as the point at which the nicotine infusion was started or the non-IV dose was administered): 5, 10, 15, 30, 60, 90 minutes, and 2, 3, 4, 5, 6, and 8 hours. Whole blood samples were centrifuged and plasma samples were then stored at −20 degrees Celsius until analysis. Plasma concentrations of nicotine were determined by gas chromatography/mass spectrometry as described by Baskin et al. (*Clin. Chem.,* 31:76–80 (1991)).

For this study, the maximum plasma nicotine concentration (Cmax) and the time to reach Cmax (Tmax) were defined as the highest measured plasma concentrations and the time of the sample, respectively. The following pharmacokinetics parameters were calculated using standard equations (Gibaldi (ed.) *Pharmcokinetics* 2nd ed, Marcel Dekker Inc., New York 409–17 (1982)): area tinder the plasma nicotine concentration versus time curve (AUC), bioavailability (F), blood elimination half-life (T½), volume of distribution (Vdss), and blood nicotine clearance (Clb).

The computed bioavailability for each subject was used in an analysis of covariance to compare the five groups. Within subject (IV versus non-IV) variation was evaluated for each group of 6 subjects using a paired-T test. In addition, data was reviewed for gender variation.

Mean plasma nicotine concentrations after IV is shown in FIG. 1. Plasma nicotine concentrations after oral, hydrophilic acidic enema, hydrophilic basic enema, hydrophobic acidic enema, and hydrophobic basic enema are shown in FIGS. 2 through 6, respectively. Nicotine was first detected in the plasma at 30 minutes with oral, hydrophilic acidic enema, and hydrophobic acidic enema administration, 10 minutes with hydrophobic basic enema administration, and 5 minutes with hydrophilic basic enema administration (when detectable levels were present).

The mean values for the pharmacokinetics parameters and statistical probability by analysis of covariance for nicotine administered by each of the various routes are shown in Table 1. No statistical differences were found in Cmax, AUC, and bioavailability when comparisons were made between enema and oral administration; however, Tmax for the hydrophilic basic enemas was significantly earlier than for the other 4 delivery systems. Finally, the mean bioavailability for the various routes of administration are as follows: oral 19%; hydrophilic acidic enema 16%; hydrophilic basic enema 14%; hydrophobic acidic enema 25%; hydrophobic basic enema 15%.

TABLE 1

|  | Subjects (n) | AUC+ (ng)(h)/mL | F % | $T_{max}$ hr | $C_{max}$ ng/mL |
|---|---|---|---|---|---|
| Oral | 6 | 9 ± 5 | 19 ± 10 | 1.1 ± 0.1 | 3 ± 1 |
| Hdrphbc Acid | 6 | 10 ± 3 | 25 ± 7 | 1.3 ± 0.2 | 3 ± 1 |
| Hdrphbc Base | 6 | 4 ± 1 | 15 ± 4 | 1.1 ± 0.5 | 2 ± 1 |
| Hrdrphlc Acid | 6 | 8 ± 4 | 16 ± 7 | 1.4 ± 0.2 | 2 ± 1 |
| Hrdrphlc Base | 6 | 4 ± 2 | 14 ± 6 | 0.3 ± 0.1 | 2 ± 1 |
| P* |  | 0.834 | 0.830 | 0.023 | 0.885 |

*Analysis of covariance adjusting for baseline.
+Analyzed on the natural log scale.
IV nicotine studies (n = 32) (mean ± SD): AUC = 12 ± 5 (ng)(hr)/mL; $C_{max}$ = 9 ± 3 ng/mL; $T_{max}$ = 0.3 ± 0.1 h.

Intraindividual side effects occurred during each study, as determined by a questionnaire filled out every 30 minutes, closely correlated with plasma nicotine concentrations. However, the threshold above which symptoms appeared varied from individual to individual with the nicotine concentration at which side effects first appeared ranging from 2.4 ng/mL to 9.9 ng/mL (although some subjects had nicotine concentrations of >11 ng/mL without symptoms). When side effects occurred, they consisted of nausea, lightheadedness, and diaphoresis with variable frequency.

The pharmacokinetics parameters T½, Vdss, and CLb calculated for IV dosing in the current study are somewhat different from those previously reported by in the literature (see, e.g., Benowitz et al., *Clin. Pharmacol. Ther.* 49:270–7 (1991)). A shorter T½ (53 (27 min.) vs. 203 (61 min.)), smaller Vdss (1.8 (0.5 L/Kg) vs 3.0 (0.7 L/Kg)), and faster CLb (106 (46 L/hr) vs. 66 (8 L/hr)) was observed in the current study. The observed differences are most likely due to the different population of subjects studied (non-smokers in the current study vs. heavy smokers in the Benowitz study), as well as the different dose of nicotine administered (0.5 mcg/Kg in the current study vs. 2 mcg/Kg in the Benowitz study). Additionally, a lower mean bioavailability was observed for the oral dose in the current study 19 (10%) as compared to that observed by Benowitz et al. (44 (9%)).

The mean bioavailability for the enema preparations was low or negligible, although there was no statistically significant difference observed when compared to oral administration. Interestingly, neither pH nor the hydrophilicity or hydrophobicity of the enema vehicle impacted significantly on absorption (although the hydrophilic basic enema had a significantly earlier Cmax). Furthermore, in the previous studies in which the nicotine patch was successfully used in active UC (Pullan et al., *NEJM* 330:811–15 (1994)), the mean plasma nicotine levels were over 12 ng/mL which is 6 fold greater than the Cmax for the enema vehicles. This suggests that large doses of nicotine could be directly administered to the colonic mucosa in UC patients and potentially yield equivalent efficacy with decreased toxicity as compared to the nicotine patch.

During the course of the study, it was observed that the systemic bioavailability of the enema vehicles appeared to be highly dependent upon the position in which the subject remained while retaining the enema. Subjects that were allowed to sit upright shortly after enema delivery were observed to have a higher bioavailability than when remaining in the left lateral decubitus position. This presumably was due to rectal pooling of the enema with absorption directly into the systemic circulation rather than the portal circulation, thereby eliminating first pass metabolism by the liver. By virtue of the positional dependence of this preparation, formulation of a colonic delivery system which could avoid direct absorption by the hemorrhoidal circulation could be beneficial.

In summary, rectal administration of nicotine had low bioavailability and was well tolerated. Therefore, nicotine may be administered to the colon as a therapeutic agent for IBD without the limitations inherent to other modes of administration.

Example 2

The aim of this study was to determine nicotine tartrate pharmacokinetics after administration by IV, and 3 mg and 6 mg eudragit S coated delay release oral (DRO) capsules.

Twenty subjects were randomly assigned to 1 to 2 groups (each n=10), 3 mg and 6 mg nicotine tartrate DRO. Each subject had 2 studies [DRO and 15 µg/kg (mean 1 mg) IV] separated by ≧1 week with the order (IV vs DRO first) randomly assigned. After nicotine administration, blood was obtained for 12 hours and serum nicotine was determined by gas chromatography/mass spectrometry. Plasma cotinine concentrations were determined HPLC in 2 subjects (both 6 mg) over 72 hours. Pharmacokinetic parameters determined were: maximum concentration (Cmax); time to Cmax (Tmax); area under the curve (AUC); bioavailability (F); volume of distribution (Vdss); clearance (CL); and half-life (T½).

Delayed-release Eudragit coated oral nicotine capsules were prepared by Tillotts Pharma AG, Ziefen, Switzerland and consisted of either 3 mg or 6 mg of nicotine (9.206 mg or 18.412 mg nicotine tartrate base salt, respectively (taking into account 7.1% water content of the tartrate salt)). The nicotine salt was suspended in an excipient (a saturated polyglycolized glyceride: Celucire 44/14 , Gautefosse France)(190 mg or 380 mg, respectively) and filled into hard galatine capsules (size 1). The capsules were then coated with Eudragit L30D. Eudragit L30D is a polymer which dissolves at about pH 6.8 in the ileum. The size of the capsule and the thickness of the Eudragit coating are similar to those used to deliver Asacol® (Eudragit coated mesalamine) to the terminal ileum (Schroeder et al., *NEJM*, 317:1625–9 (1987)).

Delayed-release Eudragit coated oral nicotine/Carbopol capsules were prepared by Tillotts Pharma. The nicotine/carbomer powder (1:50-nicotine:carbomer) was coated with Eudragit S. The coated powder was filled into hard gelatine capsules (size 1) and the capsules were coated with Eudragit S. The capsules contain 150 mg nicotine/carbomer complex, equivalent to 3 mg nicotine base.

The results of the study are shown in Table 2.

TABLE 2

| Group | No. | AUC ng*h/mL | F % | Cmax ng/mL | Tmax h | Vdss L/kg | CL L/kg/h | T½ h |
|---|---|---|---|---|---|---|---|---|
| 3 mg | 10 | 21 ± 15 | 41 ± 30 | 7 ± 6 | 4.8 ± 1.5 | | | |
| 6 mg | 10 | 42 ± 20 | 42 ± 20 | 10 ± 4 | 5.3 ± 1.1 | | | |
| IV 1 mg | 20 | 20 ± 11 | 100 ± 0 | 10 ± 2 | 0.4 ± 0.1 | 2 ± 1 | 1 ± 1 | 1 ± 1 |
| P | | 0.02 | 0.93 | 0.18 | 0.38 | | | |

The ratios of cotinine AUC after 6 mg DRO and IV nicotine were 1.5 (2036/1401) and 1.6 (3176/2002) for the 2 subjects undergoing cotinine pharmacokinetics, demonstrating significant first pass metabolism.

The results show that nicotine tartrate administered to the ileocolon by the DRO route reduced systemic bioavailability of nicotine, apparently as a result of first pass metabolism to cotinine. Since systemic cotinine is a less active metabolite than nicotine, this could partly explain the reduced side-effects achieved with the invention.

Example 3

Eight normal healthy volunteers and 8 patients with active UC were enrolled in this open label, single dose study; their characteristics are shown in Table 3. Six of 8 normal subjects were lifelong non smokers compared to 2 of 8 with colitis. Severity of colitis was based on sigmoidoscopic appearance; patients included in this study had visible contact haemorrhages or more severe changes, grade 2 or more according to Dick et al Gut 1964;5:437–42). The median sigmoidoscopic score was 2, range 2 to 3 and the median stool frequency was 4/day, range 1 to 12. All patients were taking additional therapy; 8 were on 5-amino salicylic acid compounds, 5 were on oral steroids with a mean dose of 12 mg prednisolone daily, range 5 to 20 mg and 4 were taking steroid enemas.

Formulation of nicotine carbomer enemas

Nicotine was first complexed with a carbomer before its administration as an enema. Carbopol 974P, from Goodrich UK, was the chosen carbomer used. Fifty grams of Carbopol powder was dispersed in 2,500 ml of deionised water and rapidly stirred in a suitable mixer with a blade type impeller. An homogeniser is unsuitable because at high speed it may shear the carbomer molecule. The powder was slowly sieved into the vortex created by the stirrer, allowing the powder to wet without producing insoluble particles. The colloidal suspension was formed whilst stirring at a slower speed over 30 minutes. One gram of l-nicotine base as the oil, Sigma Chemicals, was diluted with 1 ml of absolute alcohol which was then added dropwise into the vortex of the suspension with continuous stirring for 1 hour. Some of the complex was then freeze dried for later analysis. Alternatively a gel could be spread on a large glass plate and dried under vacuum at 50° C. for 24 hours. The resulting white crystalline material can then be crushed to a fine powder.

Enemas were formulated which contained 2, 6 and 12 mg of nicotine 400 mg of Carbopol, 100 mg of xanthan gum (Keltrol) to increase viscosity, 150 mg methyl hydroxybenzoate and 15 mg propyl hydroxybenzoate and deionised water to make up to 100 ml; phosphate buffer (pH 7.5) was added to produce a final pH of 5.5 with the effect of to increasing nicotine's stability. The nicotine content of sample enemas was first confirmed by diluting a small volume of the contents in dilute hydrochloric acid to produce an approximate concentration of 30 ng/ml, which could then be accurately measured by our assay.

The chemical composition of the nicotine carbomer complex was confirmed as follows. Fourier transform infrared (FTIR) spectroscopy was performed to analyse freeze dried nicotine carbomer complex as well as the starting materials, l-nicotine base and Carbopol 974P. The adsorbencies of these materials were consistent with the presence of a new compounds, not merely a mixture of the starting materials. Thin layer chromatography with spots of the free materials and the complex showed the l-nicotine moved freely and the polymer was immobile, whilst nicotine in the carbomer complex remained largely confined to the baseline spot.

$^1$H Nuclear Magnetic Resonance (NMR) was only of limited value because of the large amount of water present, the relatively small proportion of nicotine and the high viscosity. Nevertheless the analysis showed considerable differences in $^1$H resonances arising from nicotine in the carbomer, compared with the $^1$H NMR spectrum of free nicotine alone. The most noticeable chemical shift differences were with the aromatic protons associated with the pyridine ring. In the free nicotine they account for the signals at 8.18 δ, 7.50 δ and 7.15 δ. However in the complexed nicotine these shifted to 8.85 δ, 8.60 δ and 8.05 δ respectively—a chance best accounted for by ring-current changes in the pyridine ring associated with protonation of the nitrogen.

During preliminary dose ranging observations with 2 subjects no side-effects were observed with 2 and 6 mgs of nicotine, but marked symptoms of nausea and lightheadedness occurred after 15 minutes with 12 mgs. On this basis the 6 mg dose was chosen for subsequent observations in all 16 subjects. It was administered after a 10 hour fast at 9 am, first warming it to body temperature; it was given slowly over 4 minutes with the subject in the left lateral decubitus position. Blood was taken from an indwelling venous cannula at times 0, 5, 15, 30, 45, 60, 120, 180, 240, 300, 360 and 480 minutes; serum obtained by centrifugation was stored at −20° C. prior to analysis. Subjects remained horizontal for 2 hours after which they mobilised. The serum nicotine and cotinine levels were measured by gas liquid chromatography.

Side-effect experienced by the subjects were recorded as absent, mild, moderate or severe. Subjects were asked to report the time, nature and severity at any symptoms, of the commencement and each hour through the study, and were questioned particularly about nausea, vomiting, lightheadedness, tremor, palpitations and headache. Blood pressure and pulse rate were also recorded each hour and when any symptoms occurred.

Time concentration curves were generated from the data using the arithmetical means of the serum concentration at each time point. The peak plasma concentration ($C_{max}$) and concentration peak times ($T_{max}$) were derived directly from the original measured variables. The area under the concentration time curves, ng.min/ml, from 0 to 480 minutes ($AUC_{0-480}$) was calculated by the trapezoidal method. The terminal elimination half-life ($t_{1/2}$) was derived from the slope of the log linear terminal phase. For the nicotine data, the area under the curve from zero to infinity ($AUC_{0,inf}$) was calculated by the trapezoidal rule and extension of the linear terminal slope. To test the robustness of the data, the area under the curve was also calculated using a one compartmental model ($AUX_{1,co}$). The pharmacokinctic analysis was performed by the Siphar, Simed France, computer programme.

Figure 7:
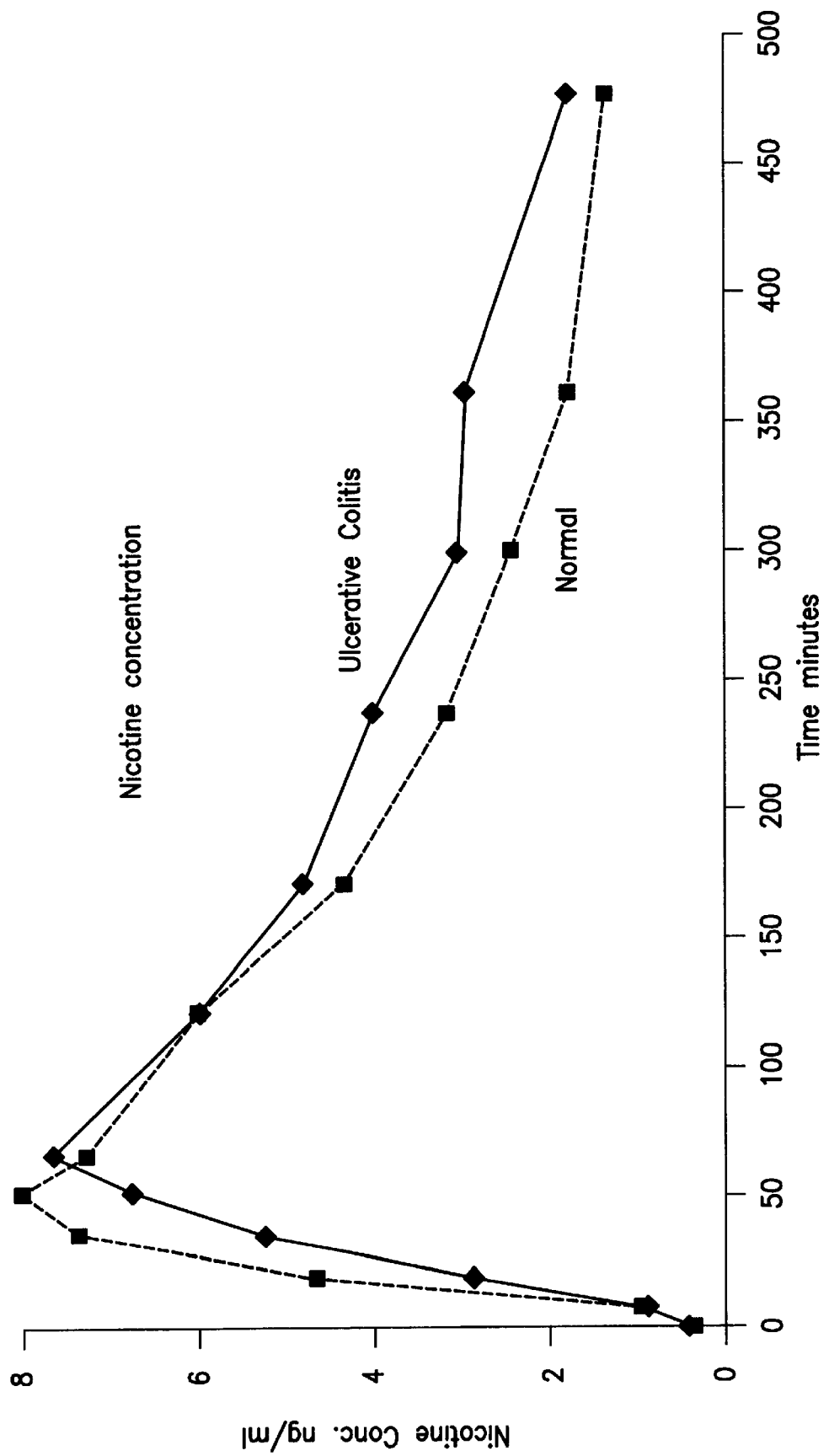
FIGS. 7 and 8 show the mean serum concentrations of nicotine and cotinine ng/ml, in 8 healthy normal volunteers and 8 patients with active ulcerative colitis over 8 hours after administration of an enema containing 6 mg of nicotine as a nicotine-carbomer complex.
Figure 8:
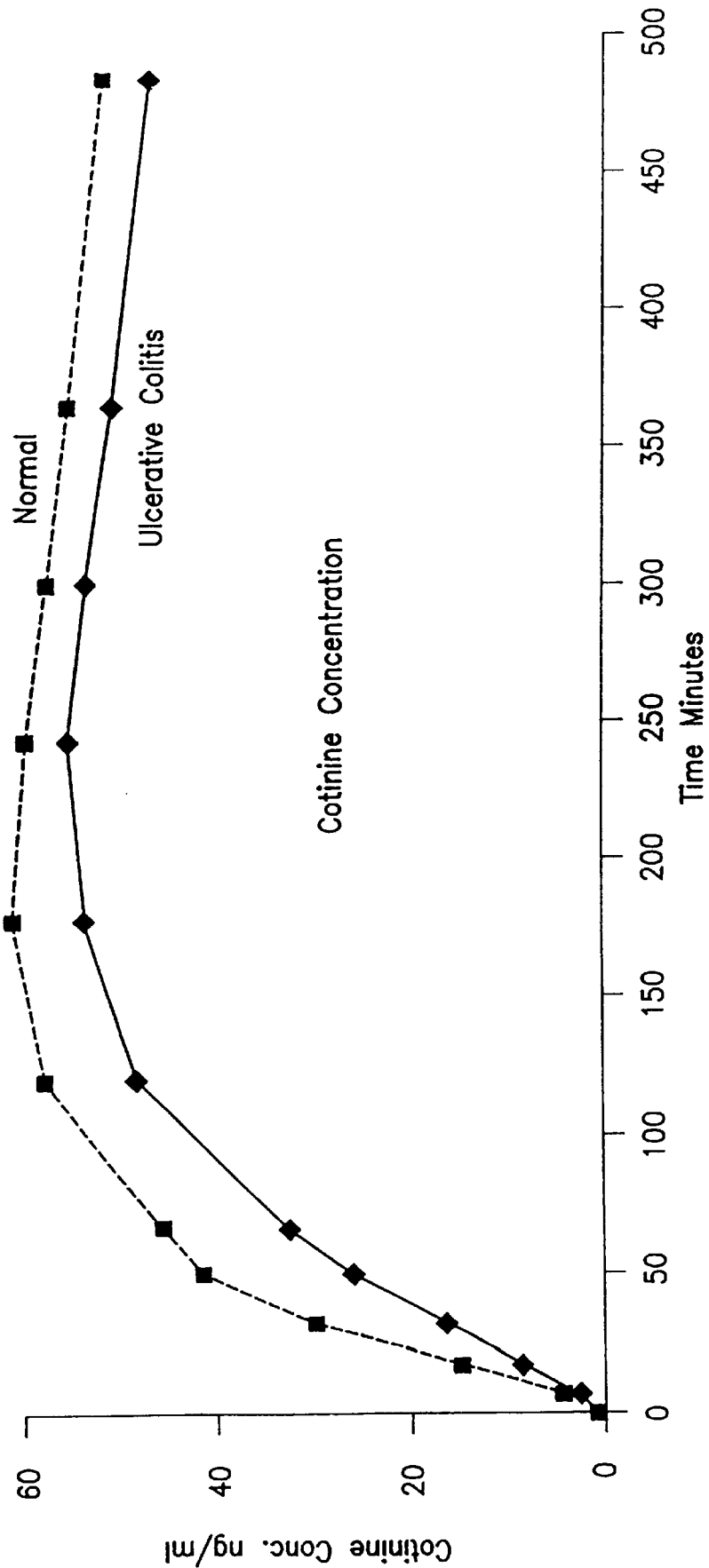

The results of the mean concentration time curves for the nicotine and cotinine levels are shown in FIGS. 7 and 8. Both nicotine and cotinine profiles were largely similar in the normal and patient groups. The pharmacokinetic parameters are shown in Table 4.

There were no statistically significant differences between normal subjects and patients with UC in any of the parameters except for the $T_{max}$ which gave median values of 45 and 60 minutes respectively (p=0.0047, Mann-Whitney).

Mean maximum concentrations of nicotine of 8.1 ng/ml were achieved after a median of 60 minutes in the total group of subjects. The mean half life of nicotine was 175 minutes±48. Mean concentrations of cotinine, the principal metabolite of nicotine, were achieved after four hours. There was considerable individual variation in the profiles for both nicotine and cotinine.

Five of the subjects, 4 normal and one patient reported side-effects. These occurred in five out of eight females and 5 of the 8 lifelong non-smokers. Those with higher $C_{max}$ values for nicotine and lower body weights were more likely to report side effects. The average onset of symptoms was about 20 minutes after administration of the enema, range 15–30 and lasted for a mean of 58 minutes, range 45–70 minutes. All 5 subjects felt lightheaded, 2 also experienced nausea and one had a headache. All symptoms were mild with the exception of one with moderate nausea; they were self limiting and not associated with changes in the pulse rate or blood pressure.

TABLE 3

Characteristics of 8 normal healthy volunteers and 8 with active ulcerative colitis given the nicotine carbomer enema

| Characteristics | Normal n = 8 | U.C. n = 8 |
|---|---|---|
| Male/female | 3/5 | 5/3 |
| Age (yrs) | | |
| Mean | 33 | 60 |
| Range | 21–46 | 34–82 |
| Height (cms) | | |
| Mean | 169 | 169 |
| Range | 160–180 | 159–180 |
| Weight (kgs) | | |
| Mean | 66 | 74 |
| Range | 57–76 | 52–102 |
| Smoking history | | |
| Lifelong non-smoker | 6 | 2 |
| Ex-smoker | 2 | 6 |

TABLE 4

Pharmacokinetic variables after administration of a single enema containing 6 mg of nicotine carbomer in 8 healthy normal volunteers, 8 patients with active UC and the total group of 16 subjects. All results expressed as mean ± SD except for $T_{max}$ which are given as median (range).

| | Normal | UC | All subjects |
|---|---|---|---|
| NICOTINE | | | |
| $C_{max}$-ng/ml | 7.8 ± 4.3 | 8.3 ± 2.7 | 8.1 ± 3.5 |
| $T_{max}$-minutes | 45 (30–60) | 60 (60–180) | 60 (30–180) |
| $AUC_{0-480}$-ng. min/ml | 1770 ± 635 | 1902 ± 1144 | 1836 ± 897 |
| $AUC_{0-inf}$-ng. min/ml | 2120 ± 819 | 2444 ± 1375 | 2281 ± 1106 |
| $AUC_{1-\infty}$-ng. min/ml | 2059 ± 827 | 2382 ± 1404 | 2221 ± 1125 |
| $t_{1/2}$-mins | 154 ± 42 | 197 ± 47 | 175 ± 48 |

TABLE 4-continued

Pharmacokinetic variables after administration of a single enema containing 6 mg of nicotine carbomer in 8 healthy normal volunteers, 8 patients with active UC and the total group of 16 subjects. All results expressed as mean ± SD except for $T_{max}$ which are given as median (range).

| | Normal | UC | All subjects |
|---|---|---|---|
| COTININE | | | |
| $C_{max}$-ng/ml | 62.7 ± 10.4 | 58.2 ± 12.9 | 60.4 ± 11.5 |
| $T_{max}$-mins | 240 (180–360) | 240 (120–300) | 240 (120–360) |
| $AUC_{0-480}$-ng. min/ml | 25707 ± 4184 | 21598 ± 4519 | 23652 ± 4712 |

The results show that of the 17 patients given nicotine enemas for 4 weeks, 3 went into full remission and 10 improved substantially. A striking feature of the clinical response was the reduced urgency and stool frequency which occurred in the first few days of treatment. The improvement continued in 5 out of the 6 who used the enemas for a further month.

Topical administration of nicotine to large bowel mucosa makes it possible to apply high concentrations at the site of inflammation, and because of the conversion of nicotine to metabolites, chiefly cotinine, during 'first pass' through the liver, only modest rises in serum nicotine occur. Strikingly side effects were few and the preparation well tolerated. The complex of nicotine with a polyacrylic carbomer delays release of the nicotine thereby further contributes to reducing any side effects.

Example 3A

The nicotine-carbomer enema of Example 3 was used in a study with patients suffering from ulcerative colitis. In an open study, 22 patients with active colitis, all non-smokers, were asked to take one 100 ml enema containing 6 mg of nicotine each night for 4 weeks. Seventeen patients completed a months treatment. Mean duration of relapse was 29 weeks, range 3–94. The patients continued taking their current oral therapy—mesalazine 17 and additional prednisolone 8, cyclosporin 1 and azathioprine 1. Symptoms with stool frequency were recorded on a diary card and an endoscopy was performed with rectal biopsy at the beginning and after 4 weeks. Sixteen of 17 improved their St. Marks score, urgency and stool frequency improved in 12, sigmoidoscopic and histological scores in 10. Three patients had a full remission of symptoms with normal sigmoidoscopy. Six of 10 with a partial response continued with the enemas for a second month and 5 showed further improvement with full remission in 2. The enema was therefore effective and produced few side effects.

Example 4

10 non-smoking adult patients with active left-sided ulcerative colitis were treated nightly for 4 weeks in an open protocol with nicotine tartrate liquid enemas at doses of 3 mg and 6 mg nicotine base. The enemas were prepared in accordance with Example 1.

Treatment consisted of one nicotine tartrate liquid enema nightly for 4 weeks. The enemas were dispensed in two doses containing 3 mg and 6 mg nicotine base. Patients were instructed to use the 3 mg liquid enemas for 1 week and then the 6 mg enemas for 3 weeks. Patients who experienced limiting adverse events (see below) while taking the 6 mg enemas on 3 consecutive days were instructed to change back to the 3 mg enemas. Patients who experienced limiting adverse events with the 3 mg enemas for 3 consecutive days were instructed to discontinue enema therapy.

A total of 10 patients who met entry criteria were enrolled in the study. Seven patients completed the 4 week study according to protocol and 3 discontinued the study within 7 days because of inability to retain the enemas. The analysis includes only the results for the 7 patients who actually completed the 4 week study (per protocol), but the data for the other 3 patients who could not retain the liquid enemas is included in the tables.

All patients had chronically active ulcerative colitis which was resistant to first line therapy (Table 5). The mean duration of symptoms was 241 days. Drug treatments utilized during the current flare of ulcerative colitis are shown in Table 1. The mean number of medical treatments failed during the current flare was 2.9±1.5 per patient, and all patients failed to respond to at least one other type of medication. Nine of 10 patients continued on at least one allowed concomitant medication during the study.

Figure 9:
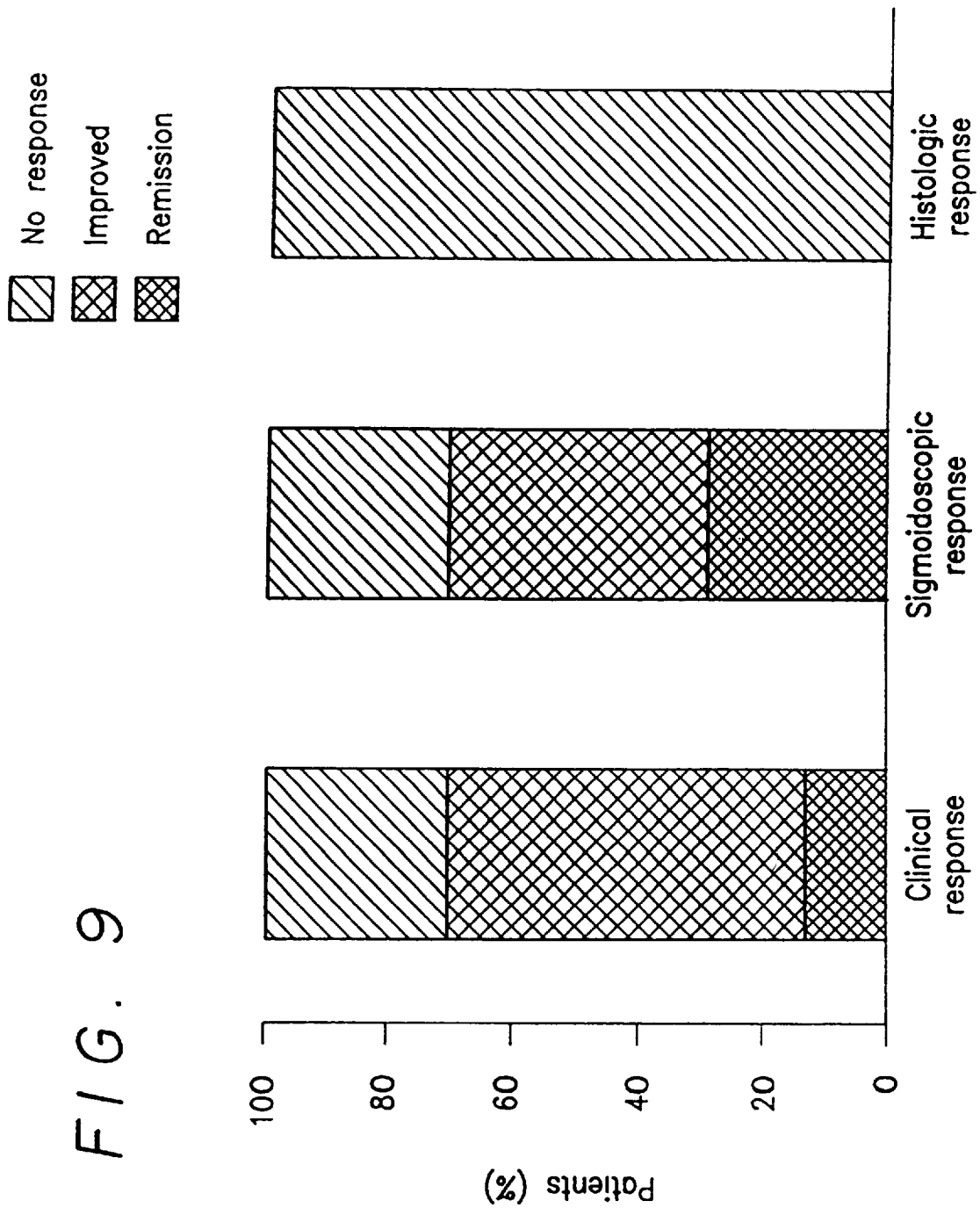
FIG. 9 shows the clinical, sigmoidoscopic and histologic response of patients administered with a nicotine tartrate enema according to example 4 (hereafter).

After 4 weeks of therapy, 4 of 7 patients had clinical improvement and 1 patient achieved clinical remission for an overall clinical response of 71% (FIG. 9). There was a statistically significant decrease in the mean±S.D. clinical disease activity index score between baseline (7.1±2.0) and week 4 (3.9±3.1), p=0.04 (paired t-test) Table 6). Similarly, after 4 weeks of therapy, 3 of 7 patients had sigmoidoscopic improvement and 2 patients achieved sigmoidoscopic remission for an overall sigmoidoscopic response of 71% (FIG. 9). There was a statistically significant decrease in the mean±S.D. sigmoidoscopic findings score between baseline (1.9±0.4) and week 4 (1.0±0.8), p=0.03 (paired t-test) (Table 2).

Adverse events occurred in 6 of 10 patients (Table 7). Three patients were unable to retain the liquid enemas because of urgency and discontinued the study within 7 days. The mean durations of enemas retention for these 3 patients there 5, 19, and 6 minutes, respectively. The remaining 7 patients who completed the 4 week study also had difficulty retaining the nicotine tartrate enemas for prolonged periods of time, the mean durations of enema retention for these patients were 39, 36, 48, 2, 53, 10 and 32 minutes. The mean±S.D. duration of nicotine tartrate enema retention for all 10 patients was 25±19 minutes.

None of the other adverse events (Table 7) were severe enough to result in discontinuation of nicotine tartrate liquid enemas therapy before the scheduled week 4 visit. All 7 patients who could retain the nicotine tartrate liquid enemas and complete the 4 week study were able to tolerate the 6 mg nicotine dose without limiting adverse events.

The peak and trough concentrations of serum nicotine and trough concentrations of plasma cotinine at 4 weeks for the 7 patients who completed the study are shown in Table 8. Only 1 out of 6 patients in whom peak and trough serum nicotine concentrations were determined had a detectable peak nicotine concentration (value 2.3 ng/mL), and all 6 patients had undetectable trough nicotine concentrations. Trough plasma cotinine concentrations were detectable in all 7 patients, but the mean±S.D. concentration was very low (13±10 ng/mL).

TABLE 5

DEMOGRAPHIC DATA IN 10 PATIENTS WITH LEFT-SIDED ULCERATIVE COLITIS

| Patient No. | Age year | Sex M/F | Former Smoker | Disease Extent cm | Disease Duration year | Duration of Flare days | Concurrent Therapy | Failed Therapy[b] |
|---|---|---|---|---|---|---|---|---|
| 1 | 35 | F | Yes | 35 | 1.8 | 660 | Prednisone 5 mg, SASP | CS Enema[c] 5ASA Enema[d] |
| 2 | 64 | M | Yes | 50 | 3.3 | 150 | 5ASA | CS Enema[d] |
| 3 | 41 | F | Yes | 50 | 2.5 | 35 | 5ASA | 5ASA Enema[d] |
| 4 | 31 | F | No | 25 | 12.0 | 210 | 5ASA | |
| 5 | 36 | F | No | 20 | 4.6 | 330 | Prednisone 20 mg, 5ASA | Olsalazine[c] 5ASA Enema[d] Azathioprine[c] |
| 6 | 34 | M | No | 30 | 13.3 | 105 | 5ASA | |
| 7 | 30 | M | No | 17 | 5.6 | 90 | 5ASA | 5ASA Enema[d] |
| 8 | 71 | M | Yes | 42 | 0.5 | 190 | Prednisone 10 mg, 5ASA | SASP[c] CS Enema[d] |
| 9 | 60 | F | Yes | 12 | 5.5 | 210 | | SASP[c] CS Enema[d] 5ASA[c] 5ASA Enema[d] |
| 10 | 68 | M | Yes | 45 | 1.2 | 425 | SASP | Prednisone[b] CS Enema[d] 5ASA[c] 5ASA Enema[d] |
| Mean | 47 | 5 M | 6 Yes | 33 | 5.0 | 241 | | |
| S.D. | 17 | 5 F | 4 No | 14 | 4.4 | 187 | | |

[a]: 5ASA indicates oral mesalamine, 5ASA enema indicates mesalamine enema, CS enema indicates corticosteroid enema, SASP indicates sulfasalazine.
[b]: Indicates other therapies failed during the current flare.
[c]: Indicates medications discontinued >14 days prior to study entry.
[d]: Indicates medications discontinued ≦14 days prior to study entry.

TABLE 6

DISEASE ACTIVITY IN 10 PATIENTS WITH LEFT-SIDED ULCERATIVE COLITIS

| Patient No. | Clinical Activity (possible values 0–13) | | Sigmodoscopic Activity (possible values 0–3) | | Histologic Activity (possible values 0–4) | |
|---|---|---|---|---|---|---|
| | Baseline | Week 4 | Baseline | Week 4 | Baseline | Week 4 |
| *Patients who completed the 4 week study* | | | | | | |
| 1 | 10 | 4 | 2 | 1 | 2 | 3 |
| 2 | 7 | 8 | 2 | 2 | 3 | 4 |
| 3 | 8 | 3 | 2 | 1 | 2 | 2 |
| 4 | 8 | 3 | 2 | 1 | 2 | 2 |
| 5 | 4 | 1 | 1 | 0 | 2 | 2 |
| 6 | 5 | 0 | 2 | 0 | 2 | 2 |
| 7 | 8 | 8 | 2 | 2 | 2 | 2 |
| Mean ± S.D. | 7.1 ± 2.0 | 3.9 ± 3.1[a] | 1.9 ± 0.4 | 1.0 ± 0.8[a] | 2.1 ± 0.4 | 2.4 ± 0.8[b] |
| *Patients unable to retain the nicotine tartrate enemas* | | | | | | |
| 8 | 9 | 9[c] | 3 | 3[c] | 3 | 3[c] |
| 9 | 6 | 6[c] | 1 | 1[c] | 3 | 3[c] |
| 10 | 7 | 7[c] | 2 | 2[c] | 3 | 3[c] |
| Mean ± S.D. | 7.3 ± 1.5 | 7.3 ± 1.5[b] | 2.0 ± 1.0 | 20 ± 10[b] | 3.0 ± 0.0 | 3.0 ± 0.0[b] |
| *Overall* | | | | | | |
| Mean ± S.D. | 7.2 ± 1.8 | 4.9 ± 3.1[b] | 1.9 ± 0.6 | 1.3 ± 0.9[b] | 2.4 ± 0.5 | 2.6 ± 0.7[h] |

[a]: Indicated p ≦0.05 (paired t-test) for baseline versus week 4.
[b]: Indicates p >0.05 (paired t-test) for baseline versus week 4.
[c]: Indicates last value carried forward.

TABLE 7

ADVERSE EVENTS AMONG 10 PATIENTS TREATED WITH NICOTINE TARTRATE LIQUID ENEMAS

| | Patient No. | | | | | | | | | | Total |
|---|---|---|---|---|---|---|---|---|---|---|---|
| | 1 | 2 | 3 | 4 | 5 | 6 | 7 | 8 | 9 | 10 | |
| Lightheadedness/Dizziness | | | | X | | X | | | | X | 3/10 |
| Nausea | | X | X | | X | | | | | | 3/10 |
| Sleep Disturbance | | | X | | | | | | | X | 2/10 |
| Shakiness/Tremor | | | | X | | | | | | | 1/10 |
| Inability to Retain Enemas | | | | | | | | X | X | X | 3/10 |
| Any Adverse Reaction | X | X | | X | X | X | | X | | X | 6/10 |

None of the adverse events were serious or life-threatening.

TABLE 8

SERUM NICOTINE AND PLASMA COTININE CONCENTRATIONS IN 7 PATIENTS AFTER 4 WEEKS OF NICOTINE TARTRATE LIQUID ENEMA THERAPY.

| Patient No. | Nicotine, ng/mL | | Cotinine, ng/mL |
|---|---|---|---|
| | Trough | Peak | Trough |
| 1 | <2.0 | 2.3 | 14 |
| 2 | <2.0 | <2.0 | 6 |
| 3 | <2.0 | <2.0 | 15 |
| 4 | <2.0 | <2.0 | 5 |
| 5 | <2.0 | <2.0 | 10 |
| 6 | <2.0 | <2.0 | 3 |
| 7 | NA | NA | 33 |
| Mean ± S.D. | | | 12 ± 10 |

NA Indicates no value available due to assay failure.

This study demonstrates that nicotine tartrate liquid enemas administered at a dose of 3 mg nicotine base/day for 1 weeks and then 6 mg for 3 weeks are safe and result in clinical improvement in non-smoking patients with mildly to moderately active, left-sided ulcerative colitis unresponsive to first-line therapy.

Example 5

A further nicotine-carbomer composition was prepared as below using triethanolamine buffer (TRIS) instead of phosphate buffer, and the nicotine plasma levels compared against the nicotine-carbomer enemas (using phosphate buffer) of Example 3 and the nicotine tartrate enemas of Example 5.

| | |
|---|---|
| Nicotine | 6 mg |
| Carbomer 974P | 400 mg |
| Keltrol | 100 mg |
| Methyl bydroxybenzoate | 150 mg |
| Propyl hydroxybenzoate | 15 mg |
| TRIS-buffer 1% w/v | 5 ml |
| Purified water to | 100 ml |
| pH | 4.5 |
| Viscosity (shear factor) | 5.95 |

Figure 10:
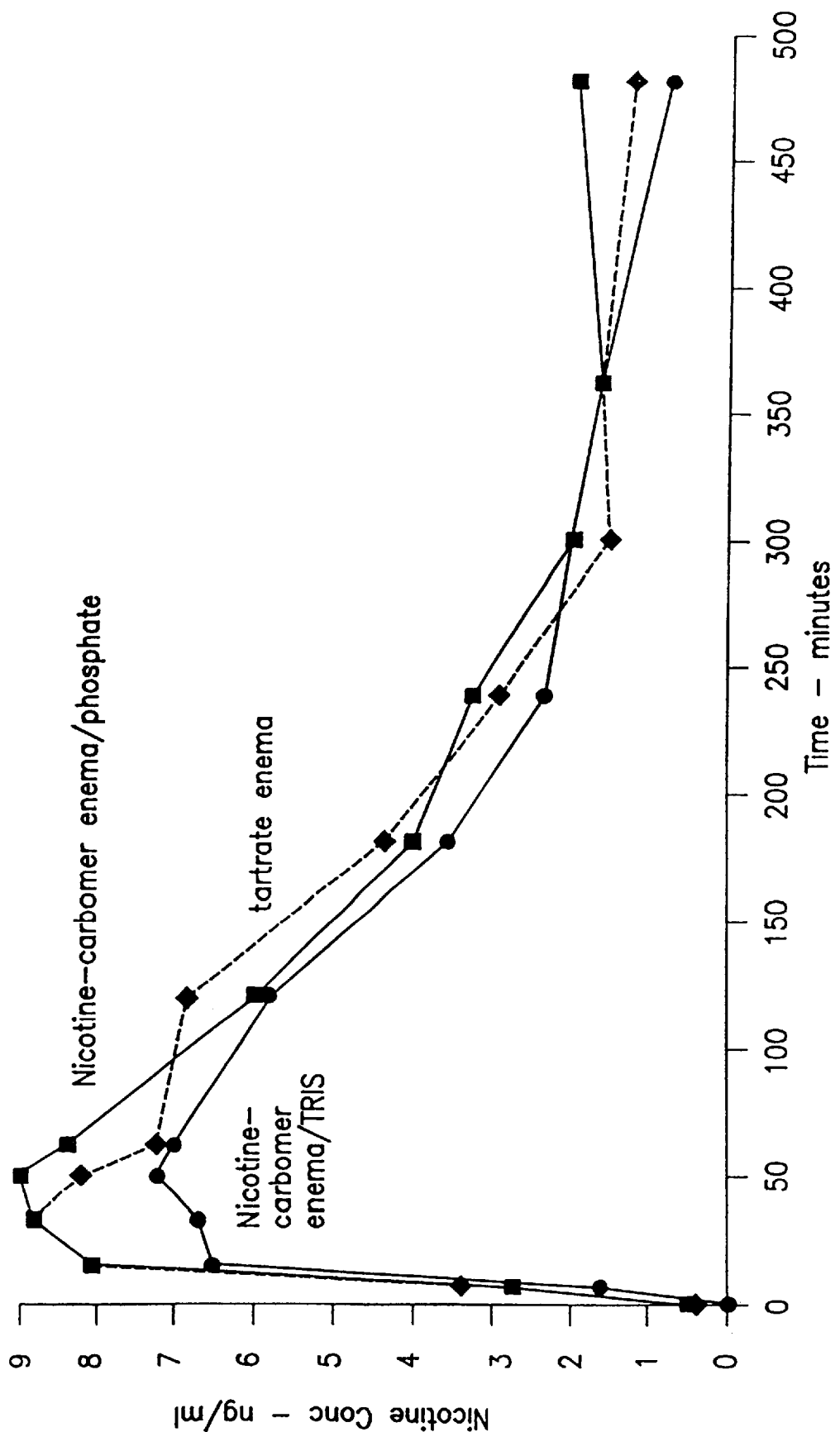

The results are shown in FIGS. 10 and 11. As can be seen the nicotine peak plasma concentration is significantly lower with the nicotine-carbomer/TRIS enema than with either of the other two-enema. Since nausea and other side effects are dependent on the peak plasma levels, this decrease further contributes to the comfort of the patient during treatment. This is evidenced by one patient, a slightly built female, who experienced some nausea with the tartrate and nicotine-carbomer/phosphate enemas, but did not experience nausea with the nicotine-carbomer/TRIS enema (FIG. 9).

In conclusion, whereas the use of nicotine gum and nicotine patch gave rise (in many patients) to intolerable side-effects, the inventors surprisingly found that delivery to the terminal ileum (oral delivery), colon (oral and rectal delivery) or rectum (rectal delivery) of this highly toxic drug not only gave an excellent clinical response (up to 70% remission, FIG. 9), but also considerably reduced the side-effects (Table 7). In contrast to the nicotine patch, very few patients stopped treatment because of intolerable side-effects. This is even more surprising because nicotine is a highly toxic drug which is not known to be topically active for IBD, and once it is delivered to the colon, there is no longer any control over its effects.

Without being bound by theory, the inventors believe that the side-effects are related to the maximum peak concentration and the rate of rise of nicotine in the systemic circulation. The low bioavailability of nicotine absorbed through the intestinal mucosa appears to be largely due to its conversion to the major metabolite cotinine on first pass metabolism in the liver. This occurs as the nicotine is taken up in the portal vein from the intestine to the liver before entering the systemic circulation.

The self-limiting toxicity discovered by the inventors as a result of colonic delivery means that high doses of nicotine can be delivered in vivo to the site of action. When the nicotine is delivered in the form of a complex with polyacrylate, the plasma levels are further limited thereby further decreasing any remaining side-effects and increasing patient comfort. More particularly when TRIS is used as a buffer in a nicotine-carbomer enema there appears to be some unexplained synergy in that the peak plasma levels and thus side-effects are minimised (FIGS. 10 and 11) so that even slightly built patients are not troubled by side-effects.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:

1. A therapeutic method of treating inflammatory bowel disease comprising locally administering to the rectum, colon and/or terminal ileum of a patient in need of such treatment, an amount of a complex of nicotine and a carbomer, effective to reduce the symptoms of said inflammatory bowel disease.

2. The method of claim 1 wherein the inflammatory bowel disease is ulcerative colitis.

3. The method of claim 1 wherein the inflammatory bowel disease is Crohn's disease.

4. The method of claim 1 wherein the inflammatory bowel disease is pouchitis.

5. The method of claim 1 wherein the complex is administered to the lower colon of said patient by rectal liquid enema.

6. The method of claim 5 wherein said enema comprises the complex in combination with a hydrophobic vehicle.

7. The method of claim 1 wherein the complex is administered to the lower colon of said patient by rectal foam enema.

8. The method of claim 1 wherein the complex is administered by means of an orally ingested post-gastric release enterically coated unit dosage form comprising an effective amount of the complex which is released from the dosage form in the ileum and/or in the colon of said patient.

9. The method of claim 1 wherein said carbomer is a Carbopol.

10. The method of claim 8 wherein the enteric coating disintegrates at about pH 7.

11. The method of claims 5 or 7 wherein a dosage of about 0.001 to about 1.5 mg of nicotine per kg body weight is administered.

12. The method of claim 11 wherein said dosage is about 0.04 to about 0.10 mg of nicotine per kg body weight.

13. The method of claim 12 wherein the total daily dosage is about 0.04 to about 0.20 mg of nicotine per kg body weight.

14. The method of claim 8 wherein a dosage of about 0.001 to about 1.5 mg of nicotine per kg body weight is administered.

15. The method of claim 14 wherein said dosage is about 0.04 to about 0.10 mg per kg body weight.

16. The method of claim 15 wherein the total daily dosage is about 0.04 to about 0.40 mg of nicotine per kg body weight.

17. A complex of nicotine and a carbomer.

18. A rectally administrable pharmaceutical enema composition comprising an amount of a complex of nicotine and a carbomer together with a pharmaceutically acceptable carrier.

19. The enema composition of claim 18 which further comprises a buffer of triethanolamine.

20. The enema composition of claim 18 wherein the amount of nicotine present is about 0.5 mg to about 10 mg.

21. A post-gastric delayed release oral enterically coated capsule comprising a complex of nicotine and a carbomer.

22. A method of preparing a carbomer-nicotine complex comprising mixing carbomer with a pharmaceutically acceptable aqueous solvent; and adding nicotine to the carbomer-solvent mixture.

23. The method of claim 22 wherein said nicotine has been dissolved in a pharmaceutically acceptable organic solvent.

24. The method of claim 23 wherein said organic solvent is an alcohol.

25. The method of claim 22 wherein said carbomer-solvent mixture is prepared by adding carbomer to the solvent; and allowing the mixture to form a colloidal suspension.

26. The method of claim 22 wherein said complex comprises the equivalent of 1 gram of nicotine per 1 to 50 grams of carbomer.

27. A therapeutic method of treating inflammatory bowel disease comprising administering to the rectum, colon and/or terminal ileum of a patient in need of such treatment an amount of a complex of nicotine and a carbomer and an amount of a compound selected from the group consisting of 5-amino salicylic acid, sulphasalazine, asalazine, prednisolone, and budesonide, said active agents being delivered in a therapeutic amount to reduce the symptoms of said inflammatory disease.

* * * * *